United States Patent
Anand et al.

(10) Patent No.: US 8,328,947 B2
(45) Date of Patent: Dec. 11, 2012

(54) METHOD FOR LOW WATER HYDROLYSIS OR PRETREATMENT OF POLYSACCHARIDES IN A LIGNOCELLULOSIC FEEDSTOCK

(75) Inventors: Vijay Kumar Anand, Ottawa (CA); Stephen Rowland, Brownsburg-Chatam (CA); Patrick Foody, Sr., Hudson (CA)

(73) Assignee: Iogen Energy Corporation, Ontario (CA)

( * ) Notice: Subject to any disclaimer, the term of this patent is extended or adjusted under 35 U.S.C. 154(b) by 573 days.

(21) Appl. No.: 12/548,718

(22) Filed: Aug. 27, 2009

(65) Prior Publication Data
US 2010/0056774 A1  Mar. 4, 2010

Related U.S. Application Data

(60) Provisional application No. 61/092,888, filed on Aug. 29, 2008.

(51) Int. Cl.
*C08B 37/00* (2006.01)
(52) U.S. Cl. .............. 127/37; 127/1; 435/105; 435/163; 435/165
(58) Field of Classification Search ............... 127/1, 37; 435/105, 163, 165
See application file for complete search history.

(56) References Cited

U.S. PATENT DOCUMENTS

| | | | |
|---|---|---|---|
| 4,427,453 A | 1/1984 | Reitter | |
| 4,461,648 A | 7/1984 | Foody | |
| 4,842,877 A | 6/1989 | Tyson | |
| 5,338,366 A | 8/1994 | Grace et al. | |
| 6,251,643 B1 | 6/2001 | Hansen et al. | |
| 6,841,042 B2 | 1/2005 | Stromberg et al. | |
| 7,347,140 B2 | 3/2008 | Scheucher et al. | |
| 7,709,042 B2 * | 5/2010 | Foody et al. | 435/105 |
| 2004/0060673 A1 | 4/2004 | Phillips et al. | |

FOREIGN PATENT DOCUMENTS

| | | |
|---|---|---|
| EP | 0 035 679 | 9/1981 |
| GB | 1 571 700 | 7/1980 |
| WO | 96/25553 | 8/1996 |
| WO | 02/070753 | 9/2002 |
| WO | 03/071025 | 8/2003 |

OTHER PUBLICATIONS

Process Design and Cost Estimate of Critical Equipment in the Biomass to Ethanol Process, Report 99-10600/15, Second-Stage Countercurrent Reactor, Final Report, Oct. 19, 2000, National Renewable Energy Laboratory, Golden Colorado.
Kim et al., "Continuous Countercurrent Extraction of Hemicellulose from Pretreated Wood Residues", Applied Biochemistry and Biotechnology, vol. 91-93 (2001) 253-67.

* cited by examiner

*Primary Examiner* — David A Reifsnyder
(74) *Attorney, Agent, or Firm* — Fitzpatrick, Cella, Harper & Scinto

(57) ABSTRACT

A method is provided for hydrolyzing polysaccharides in a lignocellulosic feedstock to produce monosaccharides or pretreating a lignocellulosic feedstock, in which an aqueous slurry of the lignocellulosic feedstock is fed into a pressurized dewatering zone wherein the feedstock is partially dewatered and then is compressed into a plug. The plug is introduced into a reaction zone that operates at a pressure ($P_r$) equal to greater than about 90 psia and under suitable temperature and pH conditions to hydrolyze the polysaccharides or pretreat the feedstock. The plug provides a pressure seal between the outlet of the dewatering zone and the reaction zone. The pressure ($P_{dwi}$) of the aqueous slurry of the lignocellulosic feedstock at the inlet of the dewatering device is related to $P_r$ as follows:

$0 \leq \Delta P <$ the lesser of [($P_r$–20 psia) and 220 psia], and
where $\Delta P$ is the absolute difference in pressure between $P_r$ and $P_{dwi}$ in psia.

41 Claims, 3 Drawing Sheets

US 8,328,947 B2

METHOD FOR LOW WATER HYDROLYSIS OR PRETREATMENT OF POLYSACCHARIDES IN A LIGNOCELLULOSIC FEEDSTOCK

FIELD OF THE INVENTION

This invention relates to an improved method for hydrolyzing polysaccharides in a lignocellulosic feedstock to produce monosaccharides and/or making the polysaccharides more accessible or susceptible to subsequent enzymatic conversion to monosaccharides. The method includes the pretreatment of lignocellulosic feedstocks to make them more amenable to enzymatic hydrolysis.

BACKGROUND OF THE INVENTION

There is increasing interest in producing fuel ethanol from lignocellulosic feedstocks such as, for example, wheat straw, corn stover, and switch grass.

One of the primary processes for producing ethanol from lignocellulosic feedstocks is to carry out a pretreatment, followed by enzymatic hydrolysis of the cellulose to glucose. The pretreatment is often carried out by exposing the feedstock to dilute sulfuric acid and high pressure steam for a short period of time. One process for doing this is steam explosion (generally disclosed in U.S. Pat. Nos. 4,461,648 and 5,916,780). Steam explosion pretreatment greatly improves the subsequent enzymatic hydrolysis of the cellulose.

Steam explosion pretreatment can be carried out in a batch or a continuous manner. Continuous operation is preferred because the productivity of the pretreatment reactor is greater than a batch reactor due to the time required to fill and empty batch reactors. In addition, there is a limit to the size at which a batch steam explosion reactor can uniformly pretreat the material. This limitation on size results in a requirement for a large number of batch steam explosion reactors in a commercial size ethanol plant.

On the other hand, a continuously-operating steam-explosion pretreatment achieves a high productivity with a good enzymatic hydrolysis of the cellulose. However, the lignocellulosic feedstock must be conveyed continuously into and through the pretreatment reactor. This may be achieved by preparing a slurry consisting of finely chopped lignocellulosic feedstock in water. The addition of water facilitates the transportation and mechanical handling of the lignocellulosic feedstock in unit operations upstream of and within the pretreatment reactor. Typically, the mass of water present is usually at least 5 to 25 times the mass of feedstock solids present for the slurry to flow uniformly.

In a conventional method of the prior art, the slurry of lignocellulosic feedstock is pressurized above the pressure in the pretreatment reactor using a series of specially engineered pumps and such slurry of lignocellulosic feedstock is heated to the reaction temperature prior to its introduction into the pretreatment reactor. This heat-up is accomplished by the injection of high pressure steam at elevated temperature. The amount of steam and acid needed for this heat-up is a direct function of the total mass of the slurry, including the water addition for transportation of the slurry. Thus, the presence of a large amount of water requires a large amount of steam for the heat-up as well as a large amount of acid. In the pretreatment reactor, the slurry is maintained at an elevated temperature for a predetermined length of time. After the pretreatment reaction is complete, the slurry of pretreated lignocellulosic feedstock is cooled by discharging it through a series of flash vessels wherein a significant amount of the original steam added can potentially be recovered as flash steam at substantially lower pressure and reused to preheat the incoming lignocellulosic feedstock slurry. Steam that could not be recovered remains as condensate in the slurry and is a source of additional dilution of the slurry.

During the downstream processing of the lignocellulosic feedstock that follows the pretreatment, substantially all the added water is removed at a significant cost by, primarily, evaporation or distillation processes. Thus, the addition of water for transportation of feedstock contributes to large steam usage, a large amount of acid usage as well as large evaporation or distillation systems that add significant capital and operating costs of the ethanol production process.

U.S. Pat. No. 4,842,877 discloses a process in which a biomass substrate is first prehydrolyzed with a reaction medium containing strong alkali and then further treated with a chelating agent to remove metal ions, thereby avoiding the formation of unwanted precipitates on process equipment. The biomass product of the chelating step is subsequently fed to a pressurized extruder reactor into which hydrogen peroxide is added, along with oxygen. The oxygen serves to activate the hydrogen peroxide while the effect of friction and pressure in the extruder accelerates the reaction of the biomass with the hydrogen peroxide. The extruder apparatus is preferably a Wenger TX-138, X-175, X-185 or X-200 continuous extrusion cooker.

U.S. Pat. No. 4,427,453 discloses an apparatus in the form of a worm feeder which consists of a conical, pressure-resistant housing having a radial charging opening at its larger diameter end and a cylindrically-shaped, axial, exit sleeve at its smaller end. The material is injected into the charging opening and is moved by a rotating conical worm under strong compression, and thus high pressure, to the smaller end where it is forced through the exit sleeve as a compressed plug. The conical housing is provided with perforations so liquid is squeezed out from the material during the compression.

U.S. Pat. No. 6,251,643 discloses a screw press having chambers for carrying out of stages of pressing and treating aqueous suspensions of material. The chambers are axially disposed in line with at least one common integral shaft having screws to convey the material. During the operation of the screw press, a plug of compacted material is formed at the exit end of each screw. This plug seals off one chamber from the next chamber.

U.S. Pat. No. 7,347,140 discloses a screw press for separation of liquid from solid/liquid mixtures, the screw press having a casing with perforations for liquid withdrawal. The casing includes a screw shaft with a circular gap through which the liquid is pressed. A counter pressure device creates a backup of the solid/liquid mixture so as to increase the pressure in the circular gap to extract more liquid from the solid/liquid mixture.

WO 96/25553 discloses a lignocellulosic dewatering system operating at atmospheric pressure to press the lignocellulosic material into an insert, which is in the form of a compact plug, whose purpose is to separate the atmospheric medium of the press from the high pressure medium in a hydrolyser.

A final report titled "Second Stage Countercurrent Reactor" prepared for the National Renewable Energy Laboratory, Golden Colo., dated Oct. 19, 2000 and published by the Harris Group discloses a first stage horizontal reactor operating at 150 psig and 185° C. and a second stage vertical reactor (also referred to as "digesters") operating at 370 psig and 225° C. An atmospheric plug screw feeder compresses pre-steamed chips to form a tight plug prior to entering the first stage, and a pressurized Tee-Pipe Assembly that provides a pressure seal for the first stage horizontal digester. In the second stage hydrolysis, a pressurized plug screw feeder compresses the pressurized, partially cooked chips from the first stage reactor to form a tight plug against the reactor pressure. A pressurized Tee-Pipe Assembly provides a pressure seal for the second-stage counter-current reactor. A pressurized shredder conveyor breaks up the plug and continuously feeds the second-stage vertical digester where the partially cooked chips from the shredder are hydrolyzed with acid.

SUMMARY OF THE INVENTION

The present invention provides an economical, continuous hydrolysis or pretreatment process, which operates with low levels of water. By operating in this manner, the invention provides significant capital and operating cost advantages in producing fermentation products, such as ethanol, from lignocellulosic feedstocks over the current processes that use a large amount of water.

Advantageously, the removal of a significant amount of water from a lignocellulosic feedstock prior to its heat-up by steam in a hydrolysis reactor reduces the steam usage and also the amount of water that needs to be removed by evaporation or distillation in downstream processing, thereby lowering capital and operating costs. A further advantageous feature of the invention is that it can result in a reduction in the amount of acid or alkali that is needed during hydrolysis or pretreatment of the feedstock.

Accordingly, one broad aspect of the present invention provides a method for hydrolyzing polysaccharides in a lignocellulosic feedstock to produce monosaccharides, comprising:
  a) providing interconnected dewatering, plug formation and reaction zones, each of the dewatering, plug formation and reaction zones being provided with an inlet zone and an outlet zone, the outlet zone of the dewatering zone being operationally associated with the inlet zone of the plug formation zone and the outlet zone of the plug formation zone being operationally associated with the inlet zone to the reaction zone, wherein the pressure ($P_r$) in the reaction zone is from about 90 to about 680 psia;
  b) feeding an aqueous slurry of the lignocellulosic feedstock to the dewatering zone to produce a partially dewatered lignocellulosic feedstock and an aqueous liquid, wherein the pressure ($P_{dwi}$) of the aqueous slurry of the lignocellulosic feedstock at the inlet zone of the dewatering zone is related to $P_r$ as follows:
  $0 \leq \Delta P <$ the lesser of $[(P_r-20$ psia$)$ and $220$ psia$]$, and
  where $\Delta P$ is the absolute difference in pressure between $P_r$ and $P_{dwi}$ in psia
  c) withdrawing, from the dewatering zone, a portion of the aqueous liquid to produce a withdrawn aqueous liquid, the withdrawn aqueous liquid being substantially free of solid lignocellulosic feedstock, and at a pressure which is lower than the of the pressure of the aqueous slurry of the lignocellulosic feedstock at the inlet zone of the dewatering zone;
  d) moving the partially dewatered lignocellulosic feedstock from the outlet zone of the dewatering zone to the inlet zone of the plug formation zone;
  e) forming a plug of lignocellulosic feedstock within the plug formation zone to provide a pressure seal between the outlet zone of the dewatering zone and the inlet zone of the reaction zone;
  f) feeding the plug of lignocellulosic feedstock from the outlet zone of the plug formation zone to the inlet zone of the reaction zone, wherein the pressure at the outlet zone of the plug formation zone is substantially the same as the pressure at the inlet zone to the reaction zone;
  g) maintaining suitable temperature and pH conditions in the reaction zone to hydrolyze polysaccharides in the lignocellulosic feedstock to produce the monosaccharides; and
  h) recovering the monosaccharides produced in step g).

Another broad aspect of the present invention provides a method for hydrolyzing polysaccharides in a lignocellulosic feedstock to produce monosaccharides, comprising:
  a) providing interconnected dewatering, plug formation and reaction zones, each of the dewatering, plug formation and reaction zones being provided with an inlet zone and an outlet zone, the outlet zone of the dewatering zone being operationally associated with the inlet zone of the plug formation zone and the outlet zone of the plug formation zone being operationally associated with the inlet zone to the reaction zone, wherein the pressure ($P_r$) in the reaction zone is from about 300 psia to about 680 psia;
  b) feeding an aqueous slurry of the lignocellulosic feedstock to the dewatering zone to produce a partially dewatered lignocellulosic feedstock and an aqueous liquid, wherein the pressure ($P_{dwi}$) of the aqueous slurry of the lignocellulosic feedstock at the inlet zone of the dewatering zone is related to $P_r$ as follows:
  $0 \leq \Delta P < 220$ psia, and
  where $\Delta P$ is the absolute difference in pressure between $P_r$ and $P_{dwi}$ in psia
  c) withdrawing, from the dewatering zone, a portion of the aqueous liquid to produce a withdrawn aqueous liquid, the withdrawn aqueous liquid being substantially free of solid lignocellulosic feedstock, and at a pressure which is lower than the of the pressure of the aqueous slurry of the lignocellulosic feedstock at the inlet zone of the dewatering zone;
  d) moving the partially dewatered lignocellulosic feedstock from the outlet zone of the dewatering zone to the inlet zone of the plug formation zone;
  e) forming a plug of lignocellulosic feedstock within the plug formation zone to provide a pressure seal between the outlet zone of the dewatering zone and the inlet zone of the reaction zone;
  f) feeding the plug of lignocellulosic feedstock from the outlet zone of the plug formation zone to the inlet zone of the reaction zone, wherein the pressure at the outlet zone of the plug formation zone is substantially the same as the pressure at the inlet zone to the reaction zone;
  g) maintaining suitable temperature and pH conditions in the reaction zone to hydrolyze polysaccharides in the lignocellulosic feedstock to produce the monosaccharides; and
  h) recovering the monosaccharides produced in step g).

According to yet another broad aspect of the invention, there is provided a method for producing a pretreated lignocellulosic feedstock comprising:
  a) providing interconnected dewatering, plug formation and reaction zones, each of the dewatering, plug formation and reaction zones being provided with an inlet zone and an outlet zone, the outlet zone of the dewatering zone being operationally associated with the inlet zone of the plug formation zone and the outlet zone of the plug formation zone being operationally associated with the inlet zone to the reaction zone, wherein the pressure ($P_r$) in the reaction zone is from about 90 to about 680 psia;

b) feeding an aqueous slurry of the lignocellulosic feedstock to the dewatering zone to produce a partially dewatered lignocellulosic feedstock and an aqueous liquid, wherein the pressure ($P_{dwi}$) of the aqueous slurry of the lignocellulosic feedstock at the inlet zone of the dewatering zone is related to $P_r$ as follows:

$0 \leqq \Delta P <$ the lesser of $[(P_r-20$ psia$)$ and 220 psia$]$, and where $\Delta P$ is the absolute difference in pressure between $P_r$ and $P_{dwi}$ in psia c) withdrawing, from the dewatering zone, a portion of the aqueous liquid to produce a withdrawn aqueous liquid, the withdrawn aqueous liquid being substantially free of solid lignocellulosic feedstock, and at a pressure which is lower than the pressure of the aqueous slurry of the lignocellulosic feedstock at the inlet zone of the dewatering zone;

d) moving the partially dewatered lignocellulosic feedstock from the outlet zone of the dewatering zone to the inlet zone of the plug formation zone;

e) forming a plug of lignocellulosic feedstock within the plug formation zone to provide a pressure seal between the outlet zone of the dewatering zone and the inlet zone of the reaction zone;

f) feeding the plug of lignocellulosic feedstock from the outlet zone of the plug formation zone to the inlet zone of the reaction zone, wherein the pressure at the outlet zone of the plug formation zone is substantially the same as the pressure at the inlet zone to the reaction zone; and g) pretreating the lignocellulosic feedstock in the reaction zone to produce the pretreated feedstock.

According to an embodiment of the invention, the aqueous slurry of the lignocellulosic feedstock has a weight ratio of water to dry lignocellulosic feedstock solids of about 5:1 to about 33:1 prior to entering the dewatering zone, preferably about 7:1 to about 24:1. The weight ratio of water to dry lignocellulosic feedstock solids may be determined at the inlet zone of the dewatering zone.

According to another embodiment of the invention, the partially dewatered lignocellulosic feedstock has a weight ratio of water to dry lignocellulosic feedstock solids of about 0.5:1 to about 5:1, preferably about 1.5:1 to about 4:1.

According to yet another embodiment of the invention, the pressure of the aqueous slurry of the lignocellulosic feedstock at the inlet of the dewatering zone is about 70 psia to about 900 psia, about 70 psia to about 800 psia, or about 140 psia to about 800 psia, or about 300 psia to about 800 psia.

In a further embodiment of the invention, the pressure of the aqueous liquid withdrawn from the dewatering zone is about 0.3 psia to about 50 psia, or about 1 psia to about 50 psia, lower than the pressure of the aqueous slurry of the lignocellulosic feedstock at the inlet zone of the dewatering zone.

According to a further embodiment of the invention, the partially dewatered lignocellulosic feedstock is heated prior to its entry into the reaction zone, in the reaction zone or a combination thereof.

According to yet a further embodiment of the invention, the partially dewatered lignocellulosic feedstock may be at least partly heated by direct steam injection prior to its entry into the reaction zone, in the reaction zone or a combination thereof.

According to yet another embodiment of the invention, the lignocellulosic feedstock is reacted in the reaction zone under acidic conditions. The pH in the reaction zone when the lignocellulosic feedstock is reacted under acidic conditions may be between 0 and about 3, or between about 0.2 and about 3, or between about 0.5 and about 3. The acid may be added to the lignocellulosic feedstock prior to the entry of the plug of the lignocellulosic feedstock into the reaction zone, in the reaction zone or a combination thereof.

In yet a further embodiment of the invention, when the lignocellulosic feedstock is reacted in the reaction zone under acidic conditions, the lignocellulosic feedstock is held in the reaction zone for a suitable time of about 10 seconds to about 20 minutes, or about 10 seconds to about 600 seconds, or about 10 seconds to about 180 seconds, and at a suitable temperature of about 180° C. to about 260° C. to hydrolyze the lignocellulosic feedstock.

When the lignocellulosic feedstock is reacted under acidic conditions, acid added to the lignocellulosic feedstock may be selected from the group consisting of sulfuric acid, sulfurous acid, hydrochloric acid, phosphoric acid or any combination thereof. Preferably, the acid is sulfuric acid.

According to another embodiment of the invention, the lignocellulosic feedstock is reacted in the reaction zone under alkaline conditions. According to such embodiment, the alkali may be selected from the group consisting of ammonia, ammonium hydroxide, potassium hydroxide, sodium hydroxide or any combination thereof. The alkali may be added to the lignocellulosic feedstock prior to the entry of the plug of the lignocellulosic feedstock into the reaction zone, in the reaction zone or a combination thereof. The pH in the reaction zone may be between about 9.5 and about 14.

According to one embodiment of the invention, the temperature in the reaction zone during reaction under alkaline conditions may be between about 135° C. and about 260° C. According to yet another embodiment of the invention, the temperature in the reaction zone during reaction under alkaline conditions may be between about 120° C. and about 220° C. and the lignocellulosic feedstock may be reacted for about 1 minute to about 120 minutes or for about 2 minutes to about 60 minutes to pretreat the lignocellulosic feedstock.

According to a further embodiment of the invention, when the lignocellulosic feedstock is reacted under alkaline conditions, the alkali is ammonia, ammonium hydroxide, or a combination thereof, the temperature in the reaction zone is between about 20° C. and about 150° C., or between about 20° C. and about 100° C., and the lignocellulosic feedstock is reacted for about 1 minutes to about 20 minutes to pretreat the lignocellulosic feedstock.

According to a further embodiment of the invention, when the lignocellulosic feedstock is reacted under alkaline conditions, the alkali is ammonia, ammonium hydroxide, or a combination thereof, the temperature in the reaction zone is between about 100° C. and about 150° C., and the lignocellulosic feedstock is reacted for about 1 minutes to about 20 minutes to pretreat the lignocellulosic feedstock.

According to yet another embodiment of the invention, when the lignocellulosic feedstock is reacted under alkaline conditions, the alkali is potassium hydroxide, sodium hydroxide, or a combination thereof, the temperature in the reaction zone is between about 100° C. and about 140° C. and the lignocellulosic feedstock is reacted for about 15 minutes to about 120 minutes to pretreat the lignocellulosic feedstock.

According to a further embodiment of the invention, the reacted lignocellulosic feedstock is cooled to a temperature equal to or less than 100° C. after it is discharged from the reaction zone. This may further involve a step of reducing the pressure of the reacted lignocellulosic feedstock to atmospheric pressure.

Yet another broad aspect of the present invention provides a system for the pretreatment or hydrolysis of a lignocellulosic feedstock including interconnected dewatering, plug formation and reaction devices, wherein the pressure ($P_r$) in the reaction device is from about 90 to about 680 psia, comprising:

a pump or pumps for pumping an aqueous slurry of the lignocellulosic feedstock into the dewatering device at a pressure between about 70 psia and about 800 psia and wherein the pressure ($P_{dwi}$) of the aqueous slurry of the lignocellulosic feedstock at the inlet of the dewatering device is related to $P_r$ as follows:

$0 \leq \Delta P <$ the lesser of [($P_r$–20 psia) and 220 psia], and where $\Delta P$ is the absolute difference in pressure between $P_r$ and $P_{dwi}$ in psia;

means within the dewatering device for removing aqueous liquid from the aqueous slurry of the lignocellulosic feedstock to form a partially dewatered lignocellulosic feedstock;

means for withdrawing aqueous liquid from within the dewatering device;

means for urging the partially dewatered lignocellulosic feedstock from the dewatering device into the plug formation device to form a plug of the lignocellulosic feedstock; and means for discharging the plug of lignocellulosic feedstock from the plug formation device and feeding the lignocellulosic feedstock into the reaction device which is at a pressure that is substantially the same as the pressure of the plug of lignocellulosic feedstock that is discharged from the plug formation device.

According to an embodiment of the invention, when the system is in operation, the aqueous slurry of the lignocellulosic feedstock is pumped into the dewatering device at a pressure between about 70 psia and about 800 psia.

According to an embodiment of the invention, the system includes means to break up the plug of lignocellulosic material prior to feeding the lignocellulosic feedstock into the reaction device.

In a further embodiment, the dewatering device and the plug formation device are integrated into a combined dewatering and plug formation device.

BRIEF DESCRIPTION OF THE DRAWINGS

In the accompanying drawings.

DETAILED DESCRIPTION OF THE INVENTION

Figure 1:
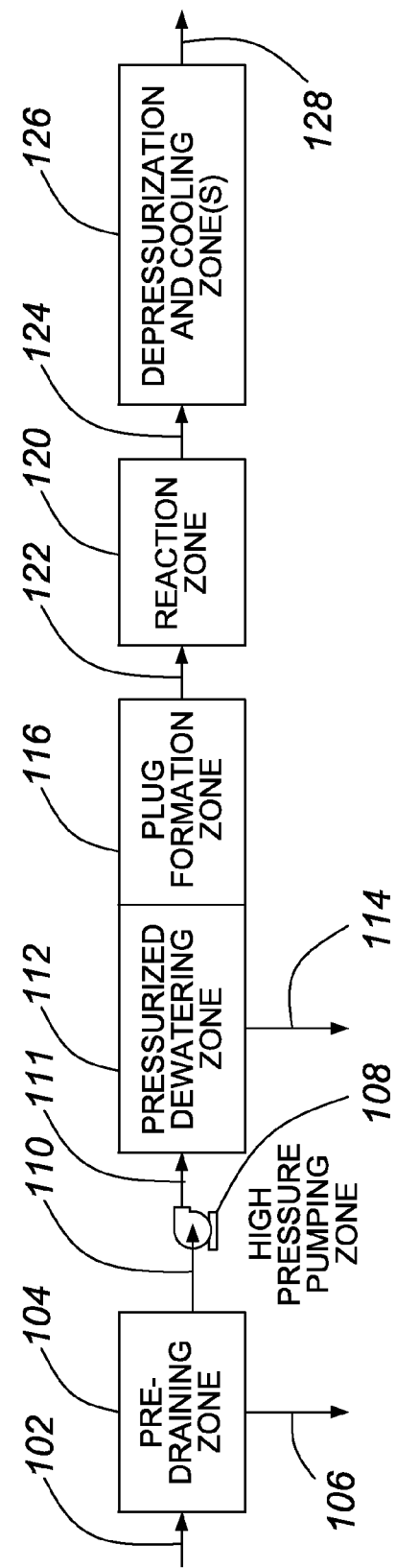
FIG. 1 is a flow diagram of a method according to an embodiment of the present invention.

The feedstock which is dewatered is a lignocellulosic material. By the term "lignocellulosic feedstock", it is meant any type of plant biomass such as, but not limited to, non-woody plant biomass, cultivated crops such as, but not limited to, grasses, for example, but not limited to, $C_4$ grasses, such as, but not limited to, switch grass, cord grass, rye grass, miscanthus, reed canary grass, or a combination thereof, sugar processing residues, for example, but not limited to, bagasse, beet pulp, or a combination thereof, agricultural residues, for example, but not limited to, soybean stover, corn stover, rice straw, rice hulls, barley straw, corn cobs, wheat straw, canola straw, oat straw, oat hulls, corn fiber, or a combination thereof, forestry biomass for example, but not limited to, recycled wood pulp fiber, sawdust, hardwood, for example aspen wood, softwood, or a combination thereof.

Furthermore, the lignocellulosic feedstock may comprise cellulosic waste material or forestry waste materials such as, but not limited to, newsprint, cardboard and the like.

Lignocellulosic feedstock may comprise one species of fiber or, alternatively, lignocellulosic feedstock may comprise a mixture of fibers that originate from different lignocellulosic feedstocks.

Lignocellulosic feedstocks comprise cellulose in an amount greater than about 20%, more preferably greater than about 30%, more preferably greater than about 40% (w/w). For example, the lignocellulosic material may comprise from about 20% to about 50% (w/w) cellulose, or any amount therebetween. The lignocellulosic feedstock also comprises lignin in an amount greater than about 10%, more typically in an amount greater than about 15% (w/w). The lignocellulosic feedstock may also comprise small amounts of sucrose, fructose and starch.

Examples of preferred lignocellulosic feedstocks include: (1) agricultural wastes such as corn stover, wheat straw, barley straw, canola straw, oat straw, rice straw and soybean stover; and (2) grasses such as switch grass, miscanthus, cord grass and reed canary grass.

Prior to dewatering, the lignocellulosic feedstock is typically subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to size reduction devices selected from the group consisting of hammer mills, tub-grinders, roll presses, refiners and hydra-pulpers. Feedstock may be reduced to particles having a length of about 1/16 to about 5 in., or any amount therebetween; for example, the length of the particles may be about 1/16, about 1/8, about 3/16, about 1/4, about 5/16, about 3/8, about 7/16, about 1/2, about 9/16, about 5/8, about 11/16, about 3/4, about 13/16, about 7/8, about 1, about 2, about 3, about 4 or about 5 in., or any amount therebetween. The length of the reduced particles may also be such that at least about 90% by weight of the particles have a length less than about 5 inches or even shorter; for example, at least about 90% by weight of the particles may have a length less than about 4, about 3, about 2, about 1 or about 1/2 inch. Washing may be carried out to remove sand, grit and other foreign particles as they can cause damage to the downstream equipment.

Prior to entering the dewatering zone, the ratio of water to lignocellulosic feedstock is adjusted to form a slurry. The aqueous slurry of the lignocellulosic feedstock can have a weight ratio of water to dry lignocellulosic feedstock solids of about 5:1 to about 33:1 or about 7:1 to about 24:1, prior to entering the dewatering zone and all ratios therebetween. For example, the weight ratio of water to dry lignocellulosic feedstock solids may be about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, about 20:1, about 21:1, about 22:1, about 23:1, about 24:1, about 25:1, about 26:1, about 27:1, about 28:1, about 29:1, about 30:1, about 31:1, about 32:1 or about 33:1. The weight ratio of water to dry lignocellulosic feedstock solids may be determined at the inlet zone of the dewatering zone. The desired weight ratio of water to dry lignocellulosic feedstock solids in the slurry is determined by factors such as pumpability, pipe-line requirements, and other practical considerations. The weight ratio of water to dry solids in an aqueous slurry, such as an aqueous slurry of lignocellulosic feedstock, or a wet material, such as a partially dewatered ligncellulosic feedstock or a plug of lignocellosic feedstock, can be determined by methods known to those of skill in the art. One method is to dry a sample of known weight of the slurry or wet material at a temperature and for a period of time that are sufficient to remove water from the sample of slurry or wet material, but do not result in thermal degradation of the solids, e.g., feedstock solids. After such water removal, or drying, the dry solids are weighed and the weight of water in the sample of slurry or wet material is the difference between the weight of the sample of slurry or wet solids and the weight of the dry solids. The amount of dry solids in an aqueous slurry may be referred to as the consistency of the slurry. Consistency may be expressed as the weight of dry solids in a weight of slurry, for example, grams per kilogram, or as a percent on a weight basis, for example, % (w/w).

By the term "operatively associated" in the present claims and specification, it is meant that an upstream zone or apparatus leads to a respective downstream zone or apparatus either directly or indirectly through an intermediate zone or apparatus.

The dewatering zone includes one or more devices to remove water under pressure from the aqueous feedstock slurry. Dewatering devices suitable for use in the invention include pressurized screw presses, as described in more detail hereinafter, and pressurized filters. Water expressed from the lignocellulosic feedstock by the dewatering step may be reused in the process, such as for slurrying the incoming feedstock.

The feedstock slurry may be fed to the pressurized dewatering device via one or more high pressure pumps, such as those available from Sulzer Corp. or Andritz AG, or by other suitable feeding device. The pump or other feeding device increases the pressure of the feedstock slurry at the inlet zone of the dewatering zone to e.g., about 70 psia to about 900 psia, or about 70 psia to about 800 psia, or more preferably about 140 psia to about 800 psia. For example, the pressure in psia of the feedstock at the inlet zone of the dewatering zone may be about 70, about 90, about 110, about 140, about 175, about 220, about 290, about 300, about 310, about 400, about 460, about 470, about 480, about 550, about 660, about 680, about 700, about 750, about 800, about 880, about 890 or about 900. The pressure may be measured with a pressure sensor located at a feedstock inlet port on the dewatering device.

The dewatering zone optionally includes a pre-draining zone in order to drain out water from the feedstock slurry at atmospheric pressure or higher. This dewatered feedstock slurry is then sent to one or more devices for dewatering the slurry under pressure.

Expressed water from the pressurized dewatering, which is substantially free of lignocellulosic feedstock, is withdrawn at a pressure that is about 0.3 psia to about 50 psia, or about 1 psia to about 50 psia, lower than the pressure of the aqueous slurry at the inlet zone of the pressurized dewatering zone. For example, the pressure of the withdrawn water from the dewatering zone may be about 0.3, about 0.5, about 0.8, about 1, about 1.5, about 2, about 3, about 4, about 5, about 7, about 10, about 15, about 20, about 25, about 30, about 35, about 40, about 45 or about 50 psia lower than the pressure of the aqueous slurry of the lignocellulosic feedstock at the inlet zone of the dewatering zone. The expressed water is withdrawn directly into one or more withdrawn water collection zones. The withdrawn water may contain other liquids that may be present in the aqueous slurry of ligncellulosic feedstock fed into the pressurized dewatering zone and expressed with the water. The collection zone(s) may be flooded with drawn water, or one or more of the collection zones may be partially filled with drawn water in which case there will be a withdrawn water surface in such collection zone(s). The pressure of the withdrawn water can be determined by measuring with a pressure sensor the pressure in the withdrawn water collection zone, or the collection zone nearest to the inlet zone of the dewatering zone if there is more than one collection zone, at an elevation that is below any withdrawn surface that may exist in such collection zone, and adjusting such pressure measurement to take into account any differential elevation head of the withdrawn water that may result from the pressure sensor being located at an elevation that is different from the elevation at which the pressure of the slurry of lignocellulosic feedstock at the inlet zone of the dewatering zone is measured. Thus, if a pressure sensor is located in the collection zone below the surface level, if any, of the withdrawn water and at an elevation that is the same as the elevation at which the pressure of the slurry of lignocellulosic feedstock at the inlet zone of the dewatering zone is measured, then no adjustment of the pressure measurement of the withdrawn water to account for differential elevation head is needed. If the pressure sensor is located at an elevation in the collection zone that is below the elevation at which the slurry of lignocellulosic feedstock at the inlet zone of the dewatering zone is measured, the pressure measurement is adjusted by adding the elevation head corresponding to the height of withdrawn water between the elevation of the pressure sensor and the elevation at which the slurry of lignocellulosic feedstock at the inlet zone of the dewatering zone is measured. Similarly, if the pressure sensor is located at an elevation in the collection zone that is above the elevation at which the slurry of lignocellulosic feedstock at the inlet zone of the dewatering zone is measured, the pressure measurement is adjusted by deducting the elevation head corresponding to the height of withdrawn water above the elevation at which the slurry of lignocellulosic feedstock at the inlet zone of the dewatering zone is measured and the elevation of the pressure sensor. Calculations of fluid elevation head are known to those of skill in the art and take into account the density of the fluid.

The withdrawn aqueous liquid preferably contains less than about 15 grams of dry lignocellulosic feedstock solids per kilogram of withdrawn aqueous liquid; that is, the withdrawn aqueous liquid may contain less than about 15, about 10, about 8, about 6, about 4, about 3, about 2 or about 1 grams of dry lignocellulosic feedstock solids per kilogram of withdrawn aqueous liquid. The amount of lignocellulosic feedstock solids in the withdrawn aqueous liquid may be determined by the method for determining the weight ratio of water to dry solids in an aqueous slurry that is described hereinabove.

The partially dewatered lignocellulosic feedstock may have a weight ratio of water to dry lignocellosic feedstock solids of about 0.5:1 to about 5:1 or about 1.5:1 to about 4:1, and all ratios therebetween, for example about 0.5:1, about 1:1, about 1.5:1, about 2:1, about 2.5:1, about 3:1, about 3.5:1, about 4:1, about 4.5:1 or about 5:1. The weight ratio of water to dry lignocellulosic feedstock solids in the partially dewatered lignocellulosic feedstock may be determined by the method described hereinabove. Alternatively, such ratio may be determined by mass balance calculations which are known to those of skill in the art. Such calculations take into account various factors such as the mass flow rate and consistency or concentration of materials fed into the dewatering zone, including but not limited to the mass flow rate and consistency of the aqueous slurry of lignocellulosic feedstock, and the mass flow rate and consistency or concentration of materials withdrawn from the dewatering zone, including but not limited to the mass flow rate and consistency of the withdrawn water.

The partially dewatered lignocellulosic feedstock from the outlet zone of the dewatering zone is moved to the inlet zone of a plug formation zone. In such zone, the partially dewatered lignocellulosic feedstock forms a plug that functions as a pressure seal between the outlet zone of the dewatering zone and the inlet zone of the reaction zone.

The partially dewatered lignocellulosic feedstock fed into the plug formation zone is at an elevated pressure that is similar to the pressure ($P_{dwi}$) of the aqueous slurry of lignocellulosic feedstock at the inlet to the pressurized dewatering zone. The pressure ($P_{dwi}$) of the aqueous slurry of the lignocellulosic feedstock at the inlet of such pressurized dewatering zone is related to the pressure ($P_r$) in a downstream reaction zone as follows:

$0 \leq \Delta P <$ the lesser of [($P_r$−20 psia) and 220 psia], and
where $\Delta P$ is the absolute difference in pressure between $P_r$ and $P_{dwi}$ in psia.

Such pressure difference results in the formation of a plug of lignocellulosic feedstock which is capable of being easily penetrated by steam. The $\Delta P$ can be any absolute pressure difference from 0 to about 220 psia and all pressure differences therebetween, for example in psia 0, about 20, about 30, about 50, about 75, about 100, about 150, about 180, about 200, about 210 or about 220.

The plug of lignocellulosic feedstock may have a weight ratio of water to dry lignocellulosic feedstock solids of about 0.5:1 to about 5:1, or about 1:1 to about 4:1, or about 1.5:1 to about 4:1, or about 1.5:1 to about 3.5:1, and all ratios therebetween, for example about 0.5:1, about 1:1, about 1.5:1, about 2:1, about 2.5:1, about 3:1, about 3.5:1, about 4:1, about 4.5:1 or about 5:1. The weight ratio of water to dry lignocellulosic feedstock solids in the plug of lignocellulosic feedstock may be determined by the method described hereinabove. Alternatively, such ratio may be determined by mass balance calculations.

The plug of lignocellulosic feedstock is then discharged from the plug formation zone and fed to a downstream reaction zone. Optionally, one or more devices to break or shred the plug and/or to heat the plug or the broken or shredded plug are positioned between the discharge of the plug formation zone and the reaction zone. The pressure at the outlet zone of the plug formation zone is substantially the same as the pressure at the inlet zone to the reaction zone. In one embodiment of the invention, the difference in pressure between the outlet zone of the plug formation zone and the inlet zone to the reaction zone is less than about 25% of the pressure at the inlet zone to the reaction zone, and may be less than about 20%, about 15%, about 10% or about 5% of the pressure at the inlet zone to the reaction zone. In another embodiment of the invention, the pressure at the outlet zone of the plug formation zone is the same as the pressure at the inlet zone to the reaction zone. The pressure at the outlet zone of the plug formation zone can be determined by measuring with a pressure sensor the pressure in a zone into which the plug is first discharged, wherein the open volume of this latter zone is such that, in operation, the density of dry lignocellulosic feedstock solids therein, expressed as kilograms of dry solids per cubic meter of open zone volume, is less than the density of dry lignocellulosic feedstock solids at the outlet zone of the plug formation zone, expressed as kilograms of dry solids per cubic meter of plug volume. Without being limiting, the aforementioned zone into which the plug is discharged may be contained in a cylindrically shaped pipe, vessel or chamber, or a part thereof, that has a cross-sectional area bounded by its internal circumference that is larger than the cross-sectional area of the surface of the plug at the outlet zone of the plug formation zone, such cross-sectional area of the plug surface being the area defined by the intersection of the plug at the outlet zone and a cross-sectional plane that is perpendicular to the direction of plug flow at the outlet zone of the plug formation zone. Other non-limiting examples of devices or chambers that may contain a zone into which the plug is discharged and that may have the requisite volume are a plug breaker, shredder, conveyor, rotary feeder or heater. The plug may be discharged directly into the inlet zone of the reaction zone. As discussed hereinafter, various types of reactors may be used to contain the reaction zone, including two or more reactors, arranged in series or parallel. The pressure at the inlet zone to the reaction zone may be measured with a pressure sensor located at a feedstock inlet port on a reactor. If two or more reactors are arranged in series, the inlet zone to the reaction zone means the inlet zone of the first reactor.

In the reaction zone, according to one embodiment of the invention, at least a portion of polysaccharides contained in the lignocellulosic feedstock is hydrolyzed to produce one or more monosaccharides. Preferably, at least a portion of the xylan contained in the lignocellulosic feedstock is hydrolyzed to produce at least xylose in a pretreatment.

The term "polysaccharides" is used herein in the conventional sense and includes but is not limited to cellulose and xylan. The term "monosaccharides" is used herein in the conventional sense, and includes those sugars released by hydrolyzing a lignocellulosic feedstock, e.g., hexose, galactose and fructose as well as the trioses, glyceraldehyde and dihydroxyacetone; the tetroses, erythrose, threose and erythrulose; the pentoses, arabinose, lyxose, ribose, deoxyribose, xylose, ribulose and xylulose; and the hexoses, allose, altrose, galactose, glucose, gulose, mannose, talose, fructose, psicose and tagatose.

If the term "oligosaccharide" is used herein, it is used in the conventional sense as a saccharide polymer containing three to ten component sugars, including fructo-oligosaccharides, galacto-oligosaccharides and manno-oligosaccharides, as well as raffinose, melibiose and maltotriose.

The pressure in the reaction zone is between about 90 psia and about 680 psia and all pressures therebetween; for example the pressure in psia may be about 90, about 100, about 120, about 150, about 200, about 240, about 250, about 270, about 280, about 290, about 300, about 350, about 400, about 450, about 500, about 550, about 580, about 590, about 600, about 650 or about 680. The pressure in the reaction zone may be measured with one or more pressure sensors. If the one or more reactors containing the reaction zone are configured in a manner such that there are different pressure levels within the reaction zone, the pressure at the location in the reaction zone where the feedstock enters the reaction zone, via the inlet zone to the reaction zone, is considered herein to be the pressure of the reaction zone.

Preferably, the lignocellulosic feedstock is treated in the reaction zone under acidic or alkaline conditions. The pH of the lignocellulosic feedstock in the reaction zone will depend on whether the reaction zone is operated under acidic or alkaline conditions. For acidic conditions, a suitable pH is from about 0 to 3 or about 0.2 to about 3 or about 0.5 to about 3 and all pH values therebetween; for example the pH may be about 0.2, about 0.3, about 0.4, about 0.5, about 1, about 1.5, about 2, about 2.5 or about 3. For alkaline conditions, a suitable pH is from about 9.5 to about 14 and all pH values therebetween; for example, the pH may be about 9.5, about 10, about 10.5, about 11, about 11.5, about 12.5, about 13, about 13.5 or about 14.

The acids added to set acidic conditions in the reaction zone may be sulfuric acid, sulfurous acid, hydrochloric acid, phosphoric acid or any combination thereof. The addition of sulfurous acid includes the addition of sulfur dioxide, sulfur dioxide plus water or sulfurous acid. Organic acids may also be used, alone or in combination with a mineral acid.

The bases added to set the alkaline conditions in the reaction zone may be ammonia, ammonium hydroxide, potassium hydroxide, sodium hydroxide or any combination thereof.

The acid, alkali or other chemical may be added prior to the entry of the plug of the lignocellulosic feedstock into the reaction zone, in the plug formation zone, in the reaction zone itself or a combination thereof. For example, acid or alkali may be added prior to the inlet of a pressurized screw press, or at the inlet to a pressurized screw press, in a dewatering zone of a pressurized screw press, in a pressurized plug screw feeder and/or in the downstream reaction zone. If one or more devices are positioned between the discharge of the plug formation zone and the reaction zone in order to break or shred the plug and/or to heat the plug or the broken or shredded plug, part or all of the acid or alkali may be added to such devices.

According to one embodiment of the invention, the reactor containing the reaction zone is a vertical reactor, including both upflow and downflow vertical reactors. In another embodiment of the invention, the reactor is a horizontal (FIG. 3) or inclined reactor. The reactor may be equipped with an internal mechanism, such as a screw (FIG. 3), conveyor or similar mechanism, for conveying the lignocellulosic feedstock within the reactor zone. The reacted feedstock may be discharged into a discharge device such as a plug screw (FIG. 3), a swept orifice discharger, a rotary discharger, a piston type discharger and the like. Two or more reactors, arranged in series or in parallel, may be used. If two or more reactors are arranged in series, the inlet zone to the reaction zone means the inlet zone of the first reactor.

A suitable temperature and time of reaction in the reaction zone will depend upon a number of variables, including the pH in the reaction zone and the degree, if any, to which hydrolysis of the polysaccharides is desired.

The partially dewatered lignocellulosic feedstock may be heated prior to its entry into the reaction zone, in the reaction zone or a combination thereof.

In one embodiment of the invention, the feedstock is subjected to a pretreatment. The term "pretreatment" or "pretreat" means a process in which the lignocellulosic feedstock is reacted under conditions which disrupts the fiber structure and that increases the susceptibility or accessibility of cellulose within the cellulosic fibers for subsequent enzymatic conversion steps, but results in modest conversion of the cellulose to glucose itself. A portion of the xylan in the lignocellulosic feedstock may be hydrolyzed to xylose and other products in a pretreatment process, although pretreatment processes that do not hydrolyze xylan are also encompassed by the invention. In embodiments of the invention, the amount of xylan hydrolyzed to xylose is more than about 50, about 60, about 70, about 80 or about 90 percent.

By the term "pretreated feedstock", it is meant a feedstock that has been subjected to pretreatment so that the cellulose contained in the cellulosic fibers has an increased susceptibility or accessibility to subsequent enzymatic conversion steps. The pretreated feedstock contains a majority or all of the cellulose that was present in the feedstock prior to pretreatment.

Pretreatment of the lignocellulosic feedstock may take place under acidic or alkaline conditions. In an acidic pretreatment process, the time in the reaction zone is from about 10 seconds to about 20 minutes or about 10 seconds to about 600 seconds or about 10 seconds to about 180 seconds and all times therebetween, for example, in seconds, about 10, about 20, about 30, about 40, about 50, about 60, about 70, about 80, about 90, about 100, about 110, about 120, about 140, about 150, about 160, about 170, about 180, about 200, about 250, about 300, about 400, about 500, about 550, about 600, about 650, about 700, about 750, about 800, about 850, about 900, about 950, about 1000, about 1050, about 1100, about 1150 or about 1200 and at a suitable temperature of about 180° C. to about 260° C. and all temperatures therebetween, for example, in degrees Celsius, about 180, about 200, about 210, about 215, about 220, about 225, about 230, about 235, about 240, about 245, about 250 or about 260. The pH for the pretreatment may be between about 0.5 and about 3, or between about 1.0 and about 2.0. For example the pH may be about 0.5, about 0.8, about 1, about 1.3, about 1.5, about 1.8, about 2.0, about 2.3, about 2.5, about 2.8 or about 3.

In an alkaline pretreatment process, the time in the reactor is from about 1 minute to about 120 minutes or about 2 minutes to about 60 minutes and all times therebetween, and at a suitable temperature of about 20° C. to about 220° C. or about 120° C. to about 220° C. and all temperatures therebetween.

Ammonia fiber expansion (AFEX), which is an alkali pretreatment method, may produce little or no monosaccharides. Accordingly, if an AFEX treatment is employed in the reaction zone, the hydrolyzate produced from the reaction zone may not yield any monosaccharides.

According to the AFEX process, the cellulosic biomass is contacted with ammonia or ammonium hydroxide, which is typically concentrated, in a pressure vessel. The contact is maintained for a sufficient time to enable the ammonia or ammonium hydroxide to swell (i.e., decrystallize) the cellulose fibers. The pressure is then rapidly reduced which allows the ammonia to flash or boil and explode the cellulose fiber structure. The flashed ammonia may then be recovered according to known processes. The AFEX process may be run at about 20° C. to about 150° C. or at about 20° C. to about 100° C. and all temperatures therebetween. The duration of this pretreatment may be about 1 minute to about 20 minutes, or any time therebetween.

Dilute ammonia pretreatment utilizes more dilute solutions of ammonia or ammonium hydroxide than AFEX. Such a pretreatment process may or may not produce any monosaccharides. Dilute ammonia pretreatment may be conducted at a temperature of about 100 to about 150° C. or any temperature therebetween. The duration for such a pretreatment may be about 1 minute to about 20 minutes, or any time therebetween.

When sodium hydroxide or potassium hydroxide are used in the pretreatment, the temperature may be about 100° C. to about 140° C., or any temperature therebetween, the duration of the pretreatment may be about 15 minutes to about 120 minutes, or any time therebetween, and the pH may be about pH 11 to about 13, or any pH value therebetween.

Alternatively, an acidic or alkaline hydrolysis process may be operated under conditions sufficiently harsh to hydrolyze cellulose to glucose and other products. For example, the amount of cellulose that is hydrolyzed to glucose and other products may be least about 40%, about 50%, about 60%, about 70%, about 80%, about 90%, about 95% or about up to 100%.

Acidic hydrolysis that is harsh enough to hydrolyze xylan and cellulose may be conducted for about 10 seconds to about 20 minutes, or any time therebetween. The temperature may be between about 180° C. and about 260° C., or any temperature therebetween. The pH may be between 0 and about 1 or any pH therebetween.

Acidic hydrolysis that is harsh enough to hydrolyze xylan and cellulose may be conducted for about 10 seconds to about 20 minutes, or any time therebetween. The temperature may be between about 180° C. and about 260° C., or any temperature therebetween. The pH may be between 0 and about 1 or any pH therebetween.

The hydrolyzed or pretreated feedstock exiting the reaction zone may be depressurized and cooled, for example to between about 30° C. and about 100° C. In one embodiment of the invention, the pressure is reduced to about atmospheric. The cooling and depressurization may be effected by one or more flash vessels.

If the hydrolyzed or pretreated feedstock exiting the reaction zone contains cellulose, it may be subjected to cellulose hydrolysis with cellulase enzymes. By the term "cellulase enzymes", "cellulase", or "enzymes", it is meant enzymes that catalyze the hydrolysis of cellulose to products such as glucose, cellobiose, and other cello-oligosaccharides. Cellulase is a generic term denoting a multienzyme mixture comprising exo-cellobiohydrolases (CBH), endoglucanases (EG) and β-glucosidases (βG) that can be produced by a number of plants and microorganisms. The process of the present invention can be carried out with any type of cellulase enzymes, regardless of their source.

Generally, a temperature in the range of about 45° C. to about 55° C., or any temperature therebetween, is suitable for most cellulase enzymes, although the temperature may be higher for thermophilic cellulase enzymes. The cellulase enzyme dosage is chosen to achieve a sufficiently high level of cellulose conversion. For example, an appropriate cellulase dosage can be about 5.0 to about 100.0 Filter Paper Units (FPU or IU) per gram of cellulose, or any amount therebetween. The FPU is a standard measurement familiar to those skilled in the art and is defined and measured according to Ghose (1987, Pure and Appl. Chem. 59:257-268). The dosage level of β-glucosidase may be about 5 to about 400 β-glucosidase units per gram of cellulose, or any amount therebetween, or from about 35 to about 100 β-glucosidase units per gram of cellulose, or any amount therebetween. The β-glucosidase unit is also measured according to the method of Ghose (supra).

The enzymatic hydrolysis of the cellulose continues for about 24 hours to about 250 hours, or any amount of time therebetween, depending on the degree of conversion desired. In one embodiment of the invention, the amount of cellulose hydrolyzed to glucose is at least about 40%, about 50%, about 60%, about 70%, about 80%, about 90%, about 95% or about 100%. The slurry thus produced is an aqueous solution comprising glucose, lignin and other unconverted, suspended solids. Other sugars that may be produced in the reaction zone may also be present in the aqueous solution. The sugars are readily separated from the suspended solids and may be further processed as required, for example, but not limited to, fermentation to produce fermentation products, including, but not limited to ethanol or butanol by yeast or bacterium. If ethanol is produced, the fermentation may be carried out with a yeast, including, but not limited to *Saccharomyces cerevisiae*.

The sugars that are subjected to the aforementioned fermentation may include not only the glucose released during cellulose hydrolysis, but also those sugars arising from a pretreatment carried out in the reaction zone, namely xylose, glucose, arabinose, mannose, galactose or a combination thereof. These sugars may be fermented together with the glucose produced by cellulose hydrolysis or they may be fed to a separate fermentation. In one embodiment of the invention, such sugars are converted to ethanol, along with the glucose from the cellulose hydrolysis, by a Saccharomyces cerevisiae yeast strain having the capability of converting both glucose and xylose to ethanol. The *Saccharomyces cerevisiae* strain may be genetically modified so that it is capable of producing this valuable byproduct (see, for example, U.S. Pat. No. 5,789,210, which is incorporated herein by reference), although it has been reported that some *Saccharomyces cerevisiae* yeast strains are naturally capable of converting xylose to ethanol.

Alternatively, prior to the enzymatic hydrolysis, the sugars arising from pretreatment are separated from the unhydrolyzed feedstock components in the pretreated feedstock slurry by washing the slurry with an aqueous solution to produce a wash stream comprising the sugars and a solids stream comprising the unhydrolyzed components. Further expedients for carrying out the separation include, but are not limited to, filtration, centrifugation, or other known processes for removing fiber solids or suspended solids. The aqueous sugar stream may then be concentrated, for example, by evaporation, with membranes, or the like. Any trace solids are typically removed by microfiltration.

In one embodiment, the aqueous sugar stream separated from the fiber solids is fermented to produce a sugar alcohol by a yeast or bacterium. The sugar alcohol may be selected from xylitol, arbitol, erythritol, mannitol and galactitol. Preferably, the sugar alcohol is xylitol. Alternatively, the sugar is converted to an alcohol, such as ethanol or butanol, by fermentation with a naturally-occurring or recombinant bacterium or fungus.

Detailed Description of FIG. 1

As seen in FIG. 1, an aqueous slurry of lignocellulosic feedstock having a consistency of about 3% to about 5% (w/w) is conveyed via pipeline 102 to a pre-draining zone 104. Here, water is drained out at atmospheric pressure or higher, through drainage line 106 to result in a first partially dewatered lignocellulosic feedstock slurry having a consistency of about 5% to about 7% (w/w). The first partially-dewatered lignocellulosic feedstock slurry exits the pre-draining zone 104 and is fed to high pressure pump 108 through line 110. High pressure pump 108 creates a high pressure zone so that the first partially-dewatered lignocellulosic feedstock slurry may be pumped via line 111 into the inlet zone of the pressurized dewatering zone 112 at high pressure, for example, at a pressure between about 70 psia and about 900 psia, or between about 70 psia and about 800 psia.

The pressurized dewatering zone 112 operates under the high pressure to express additional water from the first partially dewatered lignocellulosic feedstock slurry to provide a second partially dewatered lignocellulosic feedstock in which the water remaining is about 0.5 to about 5 or, more preferably, about 1.5 to about 4, times the weight of the dry lignocellulosic feedstock solids. The expressed water, which is substantially free of lignocellulosic feedstock, is withdrawn and collected at a pressure which is about 0.3 psia to about 50 psia less than the pressure of the aqueous slurry of first partially dewatered lignocellulosic feedstock at the inlet zone of pressurized dewatering zone 112 and is controllably drained off through drainage line 114. The withdrawn water contains less than about 15 grams of dry lignocellulosic feedstock solids per kilogram of withdrawn water. The amount of dry lignocellulosic feedstock solids contained in the withdrawn water is determined by collecting a sample of withdrawn water from, e.g., drainage line 114, and using the method described hereinabove to determine the weight ratio of water to dry solids in the sample. This second, partially dewatered lignocellulose feedstock is urged into a plug formation zone 116. As noted above, the dewatering zone is at elevated pressure. The pressure ($P_{dwi}$) of the aqueous slurry of the lignocellulosic feedstock at the inlet of the pressurized dewatering zone 112 is related to the pressure ($P_r$) in a downstream reaction zone as follows:

$0 \leq \Delta P <$ the lesser of [($P_r$–20 psia) and 220 psia], and where $\Delta P$ is the absolute difference in pressure between $P_r$ and $P_{dwi}$ in psia.

In the plug formation zone 116, the second partially dewatered lignocellulosic feedstock is formed into a plug that acts as a pressure seal between the pressurized dewatering zone and a downstream reaction zone. The plug is discharged from the plug formation zone 116 and is led to a reaction zone 120 through an appropriately sized exit line 122. The reaction zone is at an elevated pressure that is equal to greater than about 90 psia and may be as high as about 680 psia. The pressure at the outlet zone of the plug formation zone is substantially the same as the pressure at the inlet zone to the reaction zone. The difference between the pressure at the outlet zone of the plug formation zone and the pressure at the inlet zone to the reactor zone may be less than about 25% of the pressure at the inlet zone to the reactor zone. For example, the difference between the pressure at the outlet zone of the plug formation zone and the pressure at the inlet zone to the reactor zone may be about 25%, about 20%, about 15%, about 10% or about 5% less than the pressure at the inlet zone to the reactor zone. The pressure at the outlet zone of the plug formation zone may be the same as the pressure at the inlet zone to the reaction zone. In reaction zone 120, the lignocellulosic feedstock is reacted under conditions that disrupt the fibre structure and hydrolyze more than fifty percent of the xylan contained in the lignocellulosic feedstock to xylose or other products. For example, the amount of the xylan that is hydrolyzed to xylose or other products may be more than about 50, about 60, about 70, about 80 or about 90 percent. One type of reactor suitable for such purpose is a pretreatment reactor operating under acidic conditions wherein the lignocellulosic feedstock is reacted for a short time, e.g., about 10 to about 180 seconds, at a suitable pH, e.g., an acid pH of about 0.5 to about 3 and at a temperature of about 180° C. to about 260° C. Alternatively, a pretreatment reactor operating under alkaline conditions may be used. The reaction zone alternatively may be operated under conditions such that most of the xylan and cellulose contained in the lignocellulosic feedstock are hydrolyzed to xylose or other products and glucose respectively.

The reacted lignocellulosic feedstock is led through line 124 to depressurizing and cooling zone(s) 126. In the depressurizing and cooling zone(s) 126, the pressure is reduced to about atmospheric and the temperature is reduced, for example to between about 30° C. and about 100° C. If the cooled reacted product contains cellulose it may then be conveyed to an enzymatic hydrolysis zone (not shown) through conveying line 128.

Figure 2:
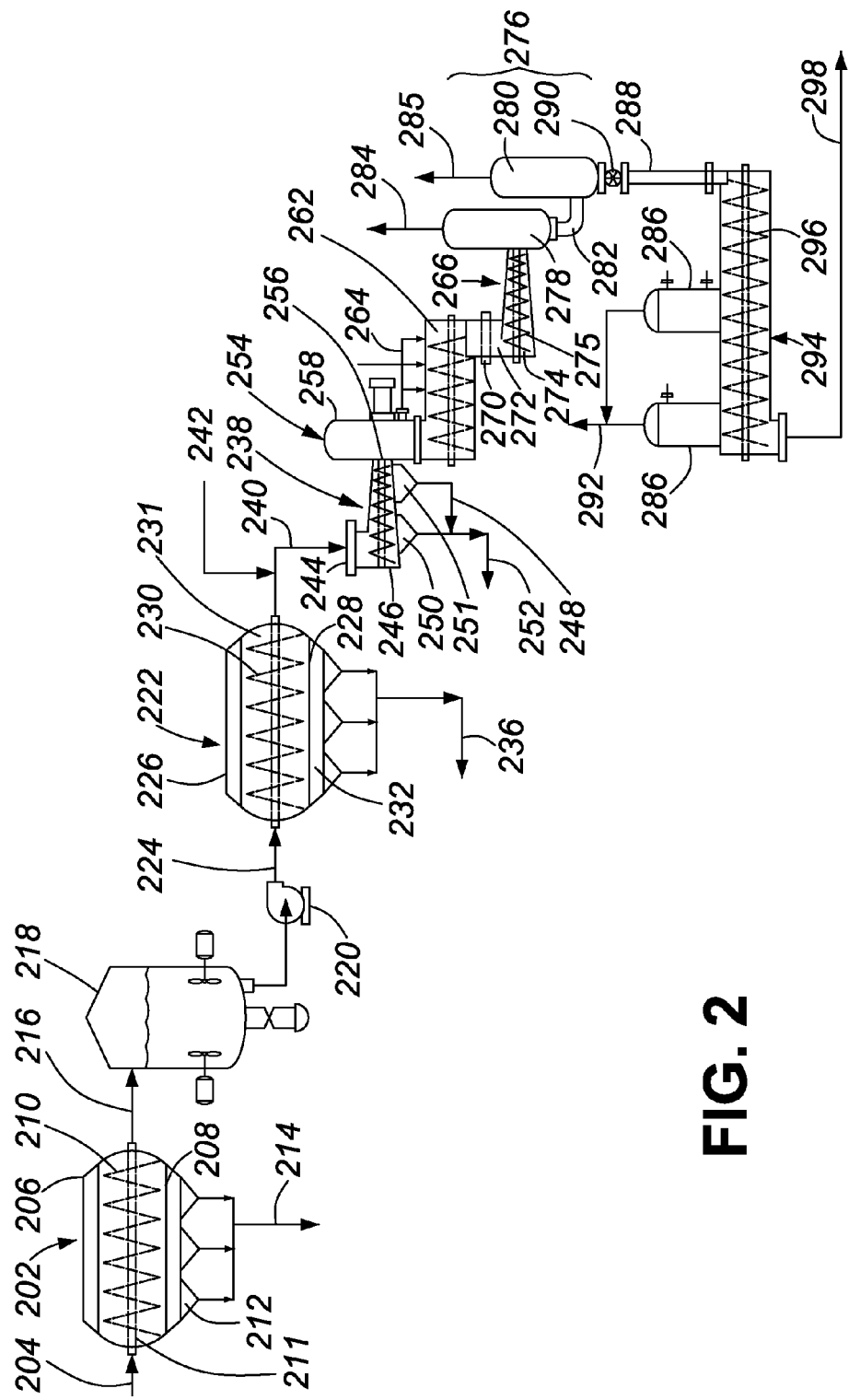
FIG. 2 is a schematic drawing of stylized apparatus according to one embodiment of the present invention for carrying out the method of the present invention.

Detailed Description of FIG. 2

The lignocellulosic feedstock is first cleaned and subjected to size reduction (not shown) to provide a suitable size e.g., about ¾ inch to about 1 inch size, or even up to 5 inch size, for mechanical handling purposes. Washing (not shown) is carried out to remove sand, grit and other foreign particles as they can cause damage to the downstream equipment. The lignocellulosic feedstock is mixed with water to form a slurry having a consistency of up to about 20% (w/w), e.g., about 3% to about 5% (w/w). The desired concentration of the feedstock in the slurry is determined by factors such as pumpability, pipe-line requirements, etc. Cleaned and slurried lignocellulosic feedstock, having a consistency of, e.g., about 3% to 5% (w/w) is stored in depots (not shown) having storage facilities similar to a silage storage bunker. These depots are strategically located around the plant such that a single pipeline can be used to transport the feedstock to the plant as well as to transport the water removed from the dewatering devices located in the plant back to the depots in a single loop. The lignocellulosic feedstock is kept in storage until the time it is needed in the plant. The lignocellulosic feedstock is transported to the pretreatment area using conventional fiber handling pumps.

As seen in FIG. 2, a slurry of such lignocellulosic feedstock is pumped into first pre-drainer 202 through line 204.

The first pre-drainer 202 is a generally-cylindrical solid shell 206 within which is a concentric screen 208 and, concentric therewith, is a screw flight 210 mounted on shaft 211. The screw flight 210, when it is rotating, moves the lignocellulosic feedstock forwardly, and also serves as a wiper that moves the drained lignocellulosic feedstock away from the screen 208 thus preventing the screen from blinding. The pre-drainer 202 also includes a lower water drainage system 212 to direct drained water through first water drainage line 214, and this drained water may be returned to the storage depot area for use in forming the slurry of the lignocellulosic feedstock.

This first partially dewatered lignocellulosic feedstock has just enough of the water drained out so that the remaining feedstock slurry can be pumped using conventional pulp handling pumps. These pumps are extensively used in the pulp and paper industry and can handle slurries containing, e.g. about 7% to about 8% (w/w) feedstock by weight and can be furnished by Sulzer Corp., Andritz AG or others. The first partially dewatered lignocellulosic feedstock containing, e.g., about 7% to about 8% (ww) feedstock is fed through feed line 216 to a surge tank 218 where it is stored until it is needed. A pump 220 draws the stored, first partially dewatered lignocellulosic feedstock from the surge tank 218 and pumps it via line 224 into the inlet zone of a pressurized dewatering press 222 at a high pressure of, e.g., about 70 psia to about 900 psia, or about 70 psia to about 800 psia, or more preferably about 140 psia to about 800 psia. Line 224 is connected to a feedstock inlet port (not shown) on pressurized dewatering press 222, and the pressure of the feedstock in the inlet zone of the dewatering zone can be measured with a pressure sensor located at the feedstock inlet port.

Pressurized dewatering press 222 consists of a generally-cylindrical solid shell 226, within which is a concentric screen 228 as well as a concentric screw flight 230 to express water out of the lignocellulosic feedstock slurry. The shell 226 is designed to withstand the pressure of the lignocellulosic slurry within the dewatering press, which may be from about 70 psia to about 900 psia, from about 70 psia to about 800 psia, or more preferably about 140 psia to about 800 psia. Water and any other liquids which have been expressed from the first partially dewatered lignocellulosic feedstock slurry are withdrawn into withdrawn water collection chamber 232, from whence it is controllably withdrawn by means (not shown) through second water drainage line 236. The surface level of withdrawn water in collection chamber 232 is above the elevation of the highest point of the concentric screen 228 and above the elevation of the pressure sensor that is used to measure the pressure of the feedstock in the inlet zone of the dewatering zone. The pressure of the withdrawn water in chamber 232 is about 0.3 psia to about 50 psia less than the pressure of the first partially dewatered lignocellulosic feedstock at the inlet to pressurized dewatering press 222. The pressure of withdrawn water in collection chamber 232 is measured with a pressure sensor located below the surface level of the withdrawn water in the chamber and at an elevation that is the same as the elevation of the pressure sensor that is used to measure the pressure of the feedstock in the inlet zone of the dewatering zone. The withdrawn water, which is substantially free of lignocellulosic feedstock, is withdrawn through line 236 and may be returned to the storage depot area for use in forming the slurry of the lignocellulosic feedstock. The withdrawn water contains less than about 15 grams of dry feedstock solids per kilogram of withdrawn water. The amount of dry lignocellulosic feedstock solids contained in the withdrawn water is determined by collecting a sample of withdrawn water from, e.g., drainage line 236, and employing the method described hereinabove to determine the weight ratio of water to dry solids in the sample. A second partially dewatered lignocellulosic feedstock is discharged from the pressurized dewatering press 222 into pressurized line 240. This second partially dewatered lignocellulosic feedstock contains water in the range of, e.g., about 0.5 to about 5 times the weight of the dry lignocellulosic feedstock solids. The weight ratio of water to dry lignocellulosic feedstock solids in the second partially dewatered lignocellulosic feedstock may be determined by collecting a sample of the feedstock from, e.g., line 240, and determining the weight ratio in the sample by the method described hereinabove. Optionally, the second partially dewatered lignocellulosic feedstock is discharged from press 222 in the form of a plug that is formed in optional plug formation zone 231. Optionally, there may be a restraining device (not shown) located at the outlet end of the plug formation zone.

The second partially dewatered lignocellulosic feedstock which is discharged into line 240 is at an elevated pressure ($P_{dwo}$). $P_{dwo}$ is similar to the pressure ($P_{dwi}$) of the first partially dewatered lignocellulosic feedstock at the inlet of the pressurized dewatering zone in pressurized dewatering press 222. $P_{dwo}$ may be equal to, less than or greater than $P_{dwi}$ depending on the design of the pressurized screw press. The second partially dewatered lignocellulosic feedstock is fed into a pressurized plug screw feeder 238 through the pressurized and appropriately sized line 240 after acid is added thereto to attain a pH of about 0.5 to about 3.0, through acid make-up line 242. Optionally, part or all of the acid may be added to the lignocellulosic feedstock prior to the inlet of the pressurized screw press 222, at the inlet to the pressurized screw press 222, in the dewatering zone of the pressurized screw press 222, in the pressurized plug screw feeder 238 and/or in a downstream pretreatment reaction zone. The pressurized plug screw feeder 238 consists of a generally-cylindrical upright hollow inlet column 244 which is operatively connected to a horizontal, generally-frusto-conical expressing chamber 246, within which is concentrically and rotatably mounted a frusto-conical screw press to express further water and other liquids from the lignocellulosic feedstock. The lignocellulosic feedstock now contains water in the range of, e.g. about 0.5 to less than about 5.0 times the weight of the dry feedstock solids. Preferably, the water content of the lignocellulosic feedstock is about 1 to about 4, or more preferably about 1.5 to about 3.5 times the weight of the dry feedstock solids. The weight ratio of water to dry lignocellulosic feedstock solids is determined by mass balance calculations that take into account the mass flow rate and consistency of the second partially dewatered lignocellulosic feedstock and the mass flow rate and composition of the acid that are fed into plug screw feeder 238, and the mass flow rate and composition of the water and other liquids that are expressed from plug screw feeder 238. A water collection system collects water which has been expressed from the lignocellulosic feedstock in collection chambers 250 and 251, from whence it is controllably withdrawn by means (not shown) through water drainage lines 252 and 248, respectively.

A plug of lignocellulosic feedstock is formed in a plug formation zone of plug screw feeder 238. As noted above, the lignocellulosic feedstock fed into the plug screw feeder is at an elevated pressure which is similar to the pressure ($P_{dwi}$) of the first partially dewatered lignocellulosic feedstock at the inlet to the pressurized dewatering zone of pressurized dewatering press 222. The pressure ($P_{dwi}$) of the aqueous slurry of the lignocellulosic feedstock at the inlet of such pressurized dewatering zone is related to the pressure ($P_r$) in a downstream reaction zone as follows:

$0 \leq \Delta P <$ the lesser of [($P_r$−20 psia) and 220 psia], and where $\Delta P$ is the absolute difference in pressure between $P_r$ and $P_{dwi}$ in psia.

Such pressure difference results in the formation of a plug of lignocellulosic feedstock which is capable of being easily penetrated by steam.

According to this embodiment, $P_{dwi}$ is the pressure of the first partially dewatered lignocellulosic feedstock at the inlet zone of the pressurized dewatering press 222. As noted above, the pressure can be measured by a pressure sensor located at the feedstock inlet port of the press.

The plug of lignocellulosic feedstock is discharged into an entry vessel 258 of a pretreatment reactor 254 by means of a pressure discharge valve system 256. There may also be a plug breaker/scraper (not shown) disposed between the discharge of the plug formation zone and the pretreatment reactor or at the inlet of the reactor. Entry vessel 258 is a generally-cylindrical upright vessel. Entry vessel 258 has a cross-sectional area bounded by its internal circumference that is larger than the cross-sectional area of the surface of the plug at its outlet from plug screw feeder 238. Such cross-sectional area of the plug surface is the area defined by the intersection of the plug at such outlet and a cross-sectional plane that is perpendicular to the direction of plug flow at such outlet. According to this embodiment, the direction of plug flow at the outlet of plug screw feeder 238 is parallel to the longitudinal axis of the frusto-conical screw press that is concentrically mounted within expressing chamber 246. The open volume of entry vessel 258 is such that the density of dry lignocellulosic feedstock solids in the vessel, expressed as kilograms of dry solids per cubic meter of open vessel volume, is less than the density of dry lignocellulosic feedstock solids at the outlet zone of the plug formation zone, expressed as kilograms of dry solids per cubic meter of plug volume. In this embodiment the pressure at the outlet zone of the plug formation zone can be determined by measuring the pressure in entry vessel 258. The pressure within entry vessel 258 can be determined by measuring with a pressure sensor the total pressure of gases (including vapors) in the vessel. The bottom of entry vessel 258 is connected to an inlet port on pretreatment reactor 254 and the pressure at the inlet port is the same as the pressure in vessel 258. Thus, in this embodiment, the pressure at the outlet zone of the plug formation zone is the same as the pressure at the inlet zone to the reaction zone. The pretreatment reactor 254 comprises a generally-cylindrical horizontal reaction chamber 262, into which high pressure steam is admitted through steam lines 264. This provides the necessary environment for the pretreatment reaction, i.e., a high pressure of about 90 psia to about 680 psia, a high temperature of about 180° C. to about 260° C. and a pH of about 0.5 to about 3. The lignocellulosic feedstock is treated in the reactor for a time of about 10 to about 180 seconds. Alternatively, the pretreatment reactor may be a vertical reactor.

The pretreated lignocellulosic feedstock is discharged from the pretreatment reactor through outlet 270 into a pressure plug vessel 266. Pressure plug vessel 266 consists of a generally-cylindrical upright entry vessel 272 which is operatively connected to a horizontal generally-frusto-conical discharging chamber 274, within which is concentrically and rotatably mounted a frusto-conical screw 275 which feeds the lignocellulosic feedstock to a series of flash vessels 276 through a pressure discharge valve system (not shown).

Flash vessel series 276 comprise a first flash vessel 278 and a second flash vessel 280 interconnected by an elbow conduit 282. Flash steam is vented from the first flash vessel 278 via vent 284. Flash steam is vented from the second flash vessel 280 via vent 285. The flash vessel series reduce the temperature in stages to about 100° C. This cooled pretreated lignocellulosic reacted product is admitted to a generally-cylindrical horizontal discharge chamber 294 which is equipped with a rotatably mounted screw conveyor 296 through connecting conduit 288 provided with a pressure lock feeding device 290. Generally-cylindrical horizontal discharge chamber 294 is operatively connected to vacuum flash vessels 286 to reduce the pressure to atmospheric by venting gases through vent lines 292. Screw conveyor 296 discharges the pretreated lignocellulosic product to cellulose hydrolysis through line 298.

Figure 3:
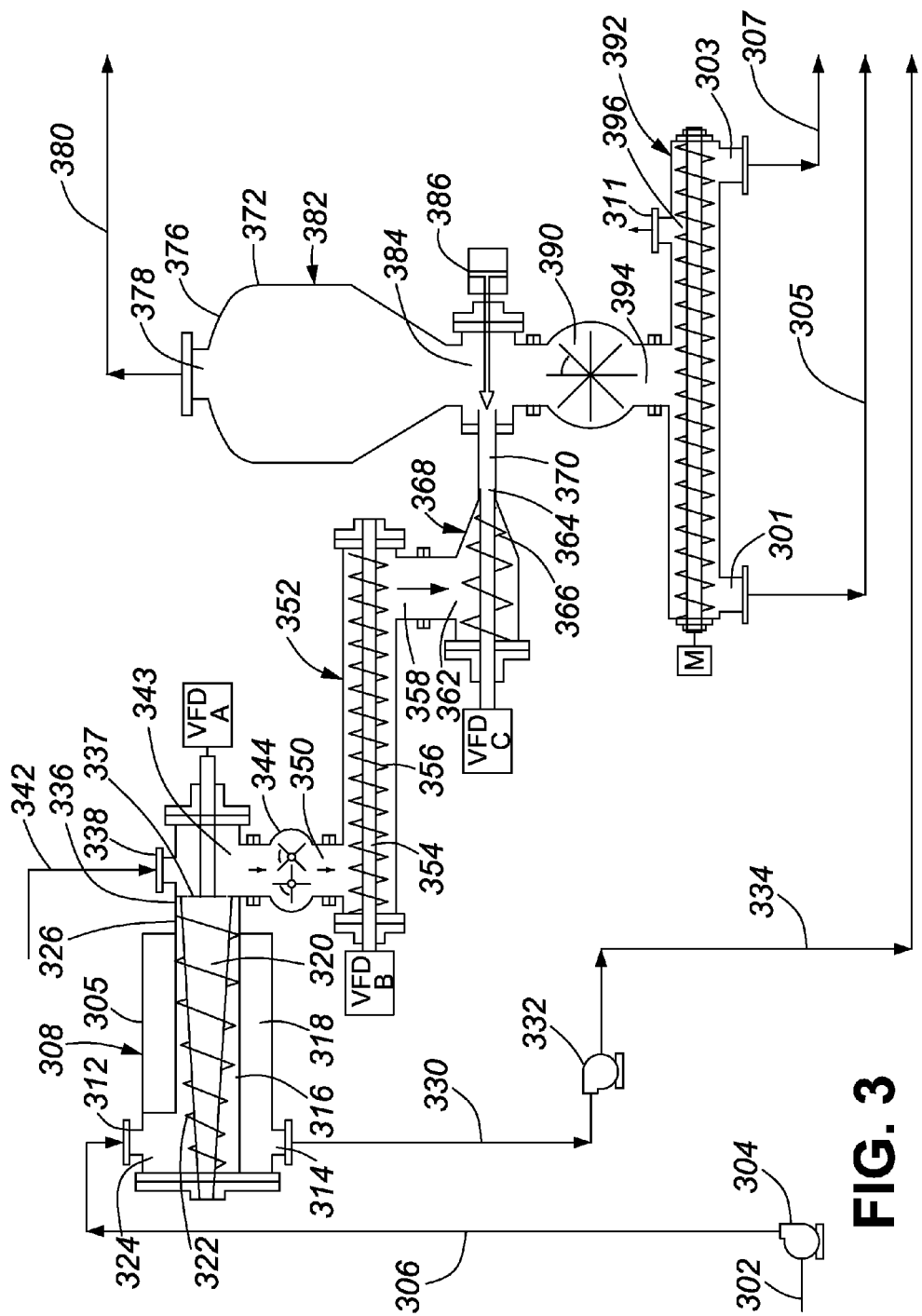
FIG. 3 is a schematic drawing of stylized apparatus according to one embodiment of the present invention for carrying out the method of the present invention The following descriptions are of preferred embodiments by way of example only and without limitation to the combination of features necessary for carrying the invention into effect.

Detailed Description of FIG. 3

As seen in FIG. 3, a slurry of lignocellulosic feedstock having a consistency of up to about 20% of feedstock by weight, e.g. about 3% to about 5% (w/w), in slurry line 302 is pumped by means of pump 304 through infeed line 306 into pressurized dewatering screw press indicated by general reference number 308. Pressurized dewatering screw press 308 comprises a generally-cylindrical solid shell 305 having a radial inlet port 312 and a radial outlet port 314. Infeed line 306 feeds lignocellulosic feedstock into screw press 308 through inlet port 312 at a pressure of, e.g., about 70 psia to about 900 psia. The pressure may be determined by measuring the pressure with a pressure sensor located at inlet port 312. A screen 316 is concentrically disposed within shell 305 to provide an annular outer space 318 between the screen and the inner circumference of shell 305. A screw 320 is concentrically and rotatably mounted within screen 316, the flights 322 of such screw being of generally constant outside diameter and attached to a frusto-conical screw shaft with a diameter that increases from the inlet end 324 to the outlet end 326 of the pressurized dewatering screw press 308. Water and any other liquids which have been expressed from the lignocellulosic feedstock slurry are withdrawn into annular space 318 which serves as a collection chamber for the withdrawn water. The surface level of withdrawn water in annular space 318 is below the elevation of the pressure sensor that is used to measure the pressure of the lignocellulosic feedstock slurry at the inlet of screw press 308. The pressure of the withdrawn water in annular space 318 is about 0.3 psia to about 50 psia less than the pressure of the feedstock slurry at the inlet of screw press 308. The pressure of withdrawn water in annular space 318 is determined by measuring pressure with a pressure sensor located below the surface level of the withdrawn water in the annular space, and adjusting such pressure measurement by adding the elevation head corresponding to the height of withdrawn water between the elevation of the pressure sensor and the elevation at which the slurry of lignocellulosic feedstock is measured with the pressure sensor located at inlet port 312. The density of withdrawn water in annular space 318 is taken into account in calculating such elevation head. The annular space 318 is connected through outlet port 314 to a turbine 332 which draws withdrawn water, which is at a pressure of lignocellulosic feedstock at the inlet end 324, through first drain line 330. The withdrawn water contains less than about 15 grams of dry feedstock solids per kilogram of withdrawn water. The amount of dry lignocellulosic feedstock solids contained in the withdrawn water is determined by collecting a sample of withdrawn water from, e.g., drain line 330, and employing the method described hereinabove to determine the weight ratio of water to dry solids in the sample. The withdrawn water, or pressate, may then be sent to a pressate return slurry make-up system (not shown) via line 334. The partially dewatered lignocellulosic feedstock exits the dewatering zone of the screw press at outlet end 326. The ratio of the weight of dry lignocellulosic feedstock solids in the partially dewatered lignocellulosic feedstock preferably is in the range of about 0.5:1 to about 5:1, and more preferably such ratio is in the range of about 1:5:1 to about 4:1. The weight ratio of water to dry lignocellulosic feedstock solids in the partially dewatered lignocellulosic feedstock may be determined by collecting a sample of the feedstock from, e.g., outlet end 326 of the screw press, and determining the weight ratio in the sample by the method described hereinabove. Alternatively, the weight ratio of water to dry lignocellulosic feedstock solids in the partially dewatered lignocellulosic feedstock may determined by mass balance calculations that take into account the mass flow rate and consistency of the lignocellulosic feedstock slurry and the mass flow rate and composition of any other material that is fed into dewatering screw press 308, and the mass flow rate and composition of the water and any other liquids that are expressed from dewatering screw press 308.

The outlet end 326 of the pressurized screw press 308 is operatively connected to a plug formation zone 336. A plug of the partially dewatered lignocellulosic feedstock is formed in the plug formation zone 336 and is discharged at plug outlet 337. There may also be a restraining device (not shown) at the plug outlet 337. The pressure ($P_{dwi}$) of the aqueous slurry of the lignocellulosic feedstock at the inlet of the dewatering device is related to the pressure ($P_r$) in a downstream reaction zone as follows:

$0 \leq \Delta P <$ the lesser of [($P_r$–20 psia) and 220 psia], and
where $\Delta P$ is the absolute difference in pressure between $P_r$ and $P_{dwi}$ in psia.

According to this embodiment, $P_{dwi}$ is the pressure at the inlet port 312 of the pressurized dewatering screw press 308.

The pressure difference ($\Delta P$) results in the formation of a plug of lignocellulosic feedstock that is capable of being easily penetrated by steam. Inlet port 338 is operatively connected to a source of steam via steam inlet line 342. The pressure of the steam is equal to or greater than the pressure ($P_r$) in the reactor zone. The plug of partially dewatered feedstock, which contains water in the range of about 0.5 to about 5 times the weight of the dry feedstock solids, is fed into a pretreatment reactor 352 via a feed chamber 343 and a lump breaker 344 to inlet port 350 of the pretreatment reactor 352. As discussed hereinafter, an acid may be added to the lignocellulosic feedstock at the inlet to the plug formation zone. If acid is not added into the plug formation zone, the weight ratio of water to dry lignocellulosic feedstock solids in the plug of partially dewatered lignocellulosic feedstock in the plug formation zone will be the same as the weight ratio of water to dry lignocellulosic feedstock solids in the partially dewatered lignocellulosic feedstock. If aqueous acid is added into the plug formation zone, the weight ratio of water to dry lignocellulosic feedstock solids in the plug of partially dewatered lignocellulosic feedstock in the plug formation zone can be determined by calculation, taking into account the weight ratio of water to dry lignocellulosic feedstock solids in the partially dewatered lignocellulosic feedstock and the amount of water that is added with the acid. The steam that is fed into the system via inlet port 338 heats the lignocellulosic feedstock and raises the temperature within the pretreatment reactor 352 to the desired level.

A drive shaft for rotating screw 320 is driven by variable frequency drive VFD A and part of the shaft goes through feed chamber. The open volume of feed chamber 343, that is, the total interior volume of the chamber less the volume of the drive shaft that is within the chamber, is such that the density of dry lignocellulosic feedstock solids in the chamber, expressed as kilograms of dry solids per cubic meter of open chamber volume, is less than the density of dry lignocellulosic feedstock solids at the outlet zone of the plug formation zone, expressed as kilograms of dry solids per cubic meter of plug volume. In this embodiment, the pressure at the outlet zone of the plug formation zone can be determined by measuring the pressure in feed chamber 343. The pressure within feed chamber 343 can be determined by measuring with a pressure sensor the total pressure of gases (including vapors) in the chamber. The pressure at the inlet to lump breaker 344 is the same as the pressure at the outlet of the lump breaker. The outlet of the lump breaker is directly connected to inlet port 350 on pretreatment reactor 254. Thus, in this embodiment, the pressure at the outlet zone of the plug formation zone is the same as the pressure at the inlet zone to the reaction zone.

Pretreatment reactor 352 comprises a generally cylindrical, horizontally-oriented vessel within which is concentrically mounted a cylindrical screw conveyor 354 having uniform flights 356. The pretreatment reactor 352 operates at a pressure of about 90 psia to about 680 psia, a pH of about 0.5 to about 3.0 and a temperature of about 180° C. to about 260° C. The lignocellulosic feedstock is treated in the reactor for a time of about 10 to about 180 seconds. The desired pH in the reactor 352 may be obtained by adding acid to the lignocellulosic feedstock prior to the inlet of the pressurized screw press, at the inlet to the pressurized screw press, in the dewatering zone of the pressurized screw press, at the inlet to the plug formation zone, between the outlet of the plug formation zone and the inlet port to the pretreatment reactor, in the pretreatment reactor or any combination of the foregoing. Preferably the acid is added to the lignocellulosic feedstock prior to the inlet of the pressurized screw press or at the inlet to the pressurized screw press in order to facilitate uniform mixing of acid and lignocellulosic feedstock prior to raising the temperature of the lignocellulosic feedstock to the pretreatment reaction temperature.

Screw conveyor 354 discharges reacted lignocellulosic feedstock through radial outlet conduit 358 into a plug screw discharger indicated by general reference number 368. The plug screw discharger 368 comprises a cylindrical inlet section 362 merging into a frusto-conical outlet section 364. Within such plug screw discharger is a frusto-conical screw conveyor 366 whose flights decrease in diameter from the inlet section 362 to the outlet section 364. The screw conveyor conveys the reacted lignocellulosic feedstock through a cylindrical outlet tube 370 which feeds into a flash vessel indicated by general reference number 382.

Flash vessel 382 comprises a cylindrical upper section 372 capped by a dome 376 and terminating in an outlet vent 378, which leads through vent line 380 to evaporators (not shown). Flash vessel 382 comprises a lower frusto-conical section that terminates in a horizontally disposed inlet section 384. The pretreated lignocellulosic feedstock is admitted to the inlet section 384 of the flash vessel 382 via cylindrical outlet tube 370 and discharge valve system 386. Flash vessel 382 operates at a lower pressure than the pressure in the pretreatment reactor 352. As pretreated lignocellulosic feedstock is admitted to the flash vessel, steam is flashed off and the pretreated lignocellulosic feedstock is cooled. Although only one flash vessel is shown in FIG. 3, two or more flash vessels, arranged in series and operating at successively lower pressures, may be used to generate flash steam at different pressures and to cool the pretreated lignocellulosic feedstock. Depressurized and cooled pretreated lignocellulosic product is discharged through discharge conduit 394 via rotary discharger 390 into reversible screw conveyor indicated by general reference number 392.

Reversible screw conveyor 392 comprises a cylindrical horizontal shell within which is mounted a reversible screw 396. Reversible screw conveyor 392 also includes two radial outlet ports 301 and 303. Outlet 301 leads to line 305 through which off-specification pretreated lignocellulosic feedstock may be removed and potentially reprocessed. Outlet 303 leads to enzymatic hydrolysis through product line 307. Reversible screw conveyor 392 also includes a vent port which vents steam, water vapor and/or gases through line 311.

We claim:
1. A method for hydrolyzing polysaccharides in a lignocellulosic feedstock to produce monosaccharides, comprising:
   a) providing interconnected dewatering, plug formation and reaction zones, each of the dewatering, plug formation and reaction zones being provided with an inlet zone and an outlet zone, the outlet zone of the dewatering zone being operationally associated with the inlet zone of the plug formation zone and the outlet zone of the plug formation zone being operationally associated with the inlet zone to the reaction zone, wherein the pressure ($P_r$) in the reaction zone is from about 90 to about 680 psia;
   b) feeding an aqueous slurry of the lignocellulosic feedstock to the dewatering zone to produce a partially dewatered lignocellulosic feedstock and an aqueous liquid, wherein the pressure ($P_{dwi}$) of the aqueous slurry of the lignocellulosic feedstock at the inlet zone of the dewatering zone is related to $P_r$ as follows:
   $0 \leq \Delta P <$ the lesser of [($P_r$–20 psia) and 220 psia], and
   where $\Delta P$ is the absolute value of the difference in pressure between $P_r$ and $P_{dwi}$ in psia
   c) withdrawing, from the dewatering zone, a portion of the aqueous liquid to produce a withdrawn aqueous liquid, the withdrawn aqueous liquid being substantially free of solid lignocellulosic feedstock, and at a pressure which is lower than the pressure of the aqueous slurry of the lignocellulosic feedstock at the inlet zone of the dewatering zone
   d) moving the partially dewatered lignocellulosic feedstock from the outlet zone of the dewatering zone to the inlet zone of the plug formation zone;

e) forming a plug of lignocellulosic feedstock within the plug formation zone to provide a pressure seal between the outlet zone of the dewatering zone and the inlet zone of the reaction zone;

f) feeding the plug of lignocellulosic feedstock from the outlet zone of the plug formation zone to the inlet zone of the reaction zone, wherein the pressure at the outlet zone of the plug formation zone is substantially the same as the pressure at the inlet zone to the reaction zone;

g) maintaining suitable temperature and pH conditions in the reaction zone to hydrolyze polysaccharides in the lignocellulosic feedstock to produce the monosaccharides; and h) recovering the monosaccharides produced in step g).

2. A method for hydrolyzing polysaccharides in a lignocellulosic feedstock to produce monosaccharides, comprising:

a) providing interconnected dewatering, plug formation and reaction zones, each of the dewatering, plug formation and reaction zones being provided with an inlet zone and an outlet zone, the outlet zone of the dewatering zone being operationally associated with the inlet zone of the plug formation zone and the outlet zone of the plug formation zone being operationally associated with the inlet zone to the reaction zone, wherein the pressure ($P_r$) in the reaction zone is from about 290 to about 680 psia;

b) feeding an aqueous slurry of the lignocellulosic feedstock to the dewatering zone to produce a partially dewatered lignocellulosic feedstock and an aqueous liquid, wherein the pressure ($P_{dwi}$) of the aqueous slurry of the lignocellulosic feedstock at the inlet zone of the dewatering zone is related to $P_r$ as follows:

$0 \leq \Delta P < 220$ psia, and where $\Delta P$ is the absolute value of the difference in pressure between $P_r$ and $P_{dwi}$ in psia c) withdrawing, from the dewatering zone, a portion of the aqueous liquid to produce a withdrawn aqueous liquid, the withdrawn aqueous liquid being substantially free of solid lignocellulosic feedstock, and at a pressure which is lower than the pressure of the aqueous slurry of the lignocellulosic feedstock at the inlet zone of the dewatering zone;

d) moving the partially dewatered lignocellulosic feedstock from the outlet zone of the dewatering zone to the inlet zone of the plug formation zone;

e) forming a plug of lignocellulosic feedstock within the plug formation zone to provide a pressure seal between the outlet zone of the dewatering zone and the inlet zone of the reaction zone;

f) feeding the plug of lignocellulosic feedstock from the outlet zone of the plug formation zone to the inlet zone of the reaction zone, wherein the pressure at the outlet zone of the plug formation zone is substantially the same as the pressure at the inlet zone to the reaction zone;

g) maintaining suitable temperature and pH conditions in the reaction zone to hydrolyze polysaccharides in the lignocellulosic feedstock to produce the monosaccharides; and h) recovering the monosaccharides produced in step g).

3. A method for hydrolyzing at least a portion of xylan in a lignocellulosic feedstock to produce xylose, comprising:

a) providing interconnected dewatering, plug formation and reaction zones, each of the dewatering, plug formation and reaction zones being provided with an inlet zone and an outlet zone, the outlet zone of the dewatering zone being operationally associated with the inlet zone of the plug formation zone and the outlet zone of the plug formation zone being operationally associated with the inlet zone to the reaction zone, wherein the pressure ($P_r$) in the reaction zone is from about 90 to about 680 psia;

b) feeding an aqueous slurry of the lignocellulosic feedstock to the dewatering zone to produce a partially dewatered lignocellulosic feedstock and an aqueous liquid, wherein the pressure ($P_{dwi}$) of the aqueous slurry of the lignocellulosic feedstock at the inlet zone of the dewatering zone is related to $P_r$ as follows:

$0 \leq \Delta P <$ the lesser of $[(P_r - 20 \text{ psia}) \text{ and } 220 \text{ psia}]$, and where $\Delta P$ is the absolute value of the difference in pressure between $P_r$ and $P_{dwi}$ in psia c) withdrawing, from the dewatering zone, a portion of the aqueous liquid to produce a withdrawn aqueous liquid, the withdrawn aqueous liquid being substantially free of solid lignocellulosic feedstock, and at a pressure which is lower than the pressure of the aqueous slurry of the lignocellulosic feedstock at the inlet zone of the dewatering zone;

d) moving the partially dewatered lignocellulosic feedstock from the outlet zone of the dewatering zone to the inlet zone of the plug formation zone;

e) forming a plug of lignocellulosic feedstock within the plug formation zone to provide a pressure seal between the outlet zone of the dewatering zone and the inlet zone of the reaction zone;

f) feeding the plug of lignocellulosic feedstock from the outlet zone of the plug formation zone to the inlet zone of the reaction zone, wherein the pressure at the outlet zone of the plug formation zone is substantially the same as the pressure at the inlet zone to the reaction zone;

g) adding acid to the partially dewatered lignocellulosic feedstock prior to the entry of the plug of the lignocellulosic feedstock into the reaction zone or to the reaction zone; and h) maintaining a temperature of between about 180° C. and about 260° C., a pH of between about 0.5 and about 3 for between about 10 seconds and about 600 seconds to hydrolyze at least a portion of xylan contained in the feedstock to xylose.

4. A method for hydrolyzing polysaccharides in a lignocellulosic feedstock to produce monosaccharides, comprising:

(a) providing one or more feed pumps and interconnected dewatering, plug formation and reaction zones, each of the dewatering, plug formation and reaction zones being provided with an inlet zone and an outlet zone, the outlet zone of the dewatering zone being operationally associated with the inlet zone of the plug formation zone and the outlet zone of the plug formation zone being operationally associated with the inlet zone to the reaction zone, wherein the pressure (Pr) in the reaction zone is from about 300 to about 680 psia;

(b) feeding an aqueous slurry of the lignocellulosic feedstock having a weight ratio of water to dry lignocellulosic feedstock solids of about 5:1 to about 33:1 via the one or more feed pumps to the dewatering zone to produce a partially dewatered lignocellulosic feedstock and an aqueous liquid, wherein the pressure (Pdwi) of the aqueous slurry of the lignocellulosic feedstock at the inlet zone of the dewatering zone is related to Pr as follows:

$0 < \Delta P < 100$ psia, and where $\Delta P$ is the absolute value of the difference in pressure between Pr and Pdwi in psia (c) withdrawing, from the dewatering zone, a portion of the aqueous liquid to produce a withdrawn aqueous liquid, the withdrawn aqueous liquid being substantially free of solid lignocellulosic feedstock, and at a pressure which is lower than the pressure of the aqueous slurry of the lignocellulosic feedstock at the inlet zone of the dewatering zone;

(d) moving the partially dewatered lignocellulosic feedstock from the outlet zone of the dewatering zone to the inlet zone of the plug formation zone;

(e) forming a plug of lignocellulosic feedstock within the plug formation zone to provide a pressure seal between the outlet zone of the dewatering zone and the inlet zone of the reaction zone, wherein the dewatering and plug formation occur in a pressurized screw press;

(f) feeding the plug of lignocellulosic feedstock from the outlet zone of the plug formation zone to the inlet zone of the reaction zone, wherein the pressure at the outlet zone of the plug formation zone is substantially the same as the pressure at the inlet zone to the reaction zone;

(g) maintaining suitable temperature and pH conditions in the reaction zone to hydrolyze polysaccharides in the lignocellulosic feedstock to produce the monosaccharides; and (h) recovering the monosaccharides produced in step g).

5. A method for producing a pretreated lignocellulosic feedstock comprising:

a) providing interconnected dewatering, plug formation and reaction zones, each of the dewatering, plug formation and reaction zones being provided with an inlet zone and an outlet zone, the outlet zone of the dewatering zone being operationally associated with the inlet zone of the plug formation zone and the outlet zone of the plug formation zone being operationally associated with the inlet zone to the reaction zone, wherein the pressure ($P_r$) in the reaction zone is from about 90 to about 680 psia;

b) feeding an aqueous slurry of the lignocellulosic feedstock to the dewatering zone to produce a partially dewatered lignocellulosic feedstock and an aqueous liquid, wherein the pressure ($P_{dwi}$) of the aqueous slurry of the lignocellulosic feedstock at the inlet zone of the dewatering zone is related to $P_r$ as follows:

$0 \leq \Delta P <$ the lesser of [($P_r$−20 psia) and 220 psia], and where $\Delta P$ is the absolute value of the difference in pressure between $P_r$ and $P_{dwi}$ in psia c) withdrawing, from the dewatering zone, a portion of the aqueous liquid to produce a withdrawn aqueous liquid, the withdrawn aqueous liquid being substantially free of solid lignocellulosic feedstock, and at a pressure that is lower than the pressure of the aqueous slurry of the lignocellulosic feedstock at the inlet zone of the dewatering zone;

d) moving the partially dewatered lignocellulosic feedstock from the outlet zone of the dewatering zone to the inlet zone of the plug formation zone;

e) forming a plug of lignocellulosic feedstock within the plug formation zone to provide a pressure seal between the outlet zone of the dewatering zone and the inlet zone of the reaction zone;

f) feeding the plug of lignocellulosic feedstock from the outlet zone of the plug formation zone to the inlet zone of the reaction zone, wherein the pressure at the outlet zone of the plug formation zone is substantially the same as the pressure at the inlet zone to the reaction zone; and g) pretreating the lignocellulosic feedstock in the reaction zone to produce the pretreated feedstock.

6. The method of claim 1, 2 or 5, wherein the aqueous slurry of the lignocellulosic feedstock has a weight ratio of water to dry lignocellulosic feedstock solids of about 5:1 to about 33:1 prior to entering the dewatering zone.

7. The method of claim 6, wherein the aqueous slurry of the lignocellulosic feedstock has a weight ratio of water to dry lignocellulosic feedstock solids of about 7:1 to about 24:1 prior to entering the dewatering zone.

8. The method of claim 7, wherein the partially dewatered lignocellulosic feedstock has a weight ratio of water to dry lignocellulosic feedstock solids of about 1.5:1 to about 4:1.

9. The method of claim 8, wherein the plug of lignocellulosic feedstock at the outlet zone of the dewatering zone has a weight ratio of water to dry lignocellulosic feedstock solids of about 1.5:1 to about 4:1.

10. The method of claim 9, wherein the pressure of the aqueous slurry of the lignocellulosic feedstock at the inlet zone of the dewatering zone is about 300 psia to about 800 psia.

11. The method of claim 10, wherein the pH in the reaction zone is between about 0.5 and about 3.0.

12. The method of claim 7, wherein the lignocellulosic feedstock is reacted in the reaction zone under acidic conditions.

13. The method of claim 12, wherein the lignocellulosic feedstock is held in the reaction zone for a suitable time of about 10 seconds to about 20 minutes at a suitable temperature of about 180° C. to about 260° C. to hydrolyze the lignocellulosic feedstock.

14. The method of claim 7, wherein the lignocellulosic feedstock is reacted in the reaction zone under alkaline conditions.

15. The method of claim 14, wherein an alkali selected from the group consisting of ammonia, ammonium hydroxide, potassium hydroxide, sodium hydroxide or any combination thereof is added to the lignocellulosic feedstock prior to the entry of the plug of the lignocellulosic feedstock into the reaction zone, in the reaction zone or a combination thereof.

16. The method of claim 15, wherein the temperature in the reaction zone is between about 120° C. and about 220° C. and the lignocellulosic feedstock is reacted for about 1 minute to about 120 minutes to pretreat the lignocellulosic feedstock.

17. The method of claim 14, wherein the pH in the reaction zone is between about 9.5 and about 14.

18. The method of claim 17, wherein the temperature in the reaction zone is between about 120° C. and about 220° C. and the lignocellulosic feedstock is reacted for about 2 minutes to about 60 minutes to pretreat the lignocellulosic feedstock.

19. The method of claim 17, wherein the alkali is ammonia, ammonium hydroxide, or a combination thereof, the temperature in the reaction zone is between about 20° C. and about 150° C. and the lignocellulosic feedstock is reacted for about 1 minute to about 20 minutes to pretreat the lignocellulosic feedstock.

20. The method of claim 19, wherein the temperature in the reaction zone is between about 100° C. and about 150° C.

21. The method of claim 17, wherein the alkali is potassium hydroxide, sodium hydroxide, or a combination thereof, the temperature in the reaction zone is between about 100° C. and about 140° C. and the lignocellulosic feedstock is reacted for about 15 minutes to about 120 minutes to pretreat the lignocellulosic feedstock.

22. The method of claim 14, wherein the temperature in the reaction zone is between about 135° C. and about 260° C.

23. The method of claim 14, wherein the alkali is ammonia, ammonium hydroxide, or a combination thereof, the temperature in the reaction zone is between about 20° C. and about 100° C. and the lignocellulosic feedstock is reacted for about 1 minute to about 20 minutes to pretreat the lignocellulosic feedstock.

24. The method of claim 7, wherein the reacted lignocellulosic feedstock is cooled to a temperature equal to or less than 100° C. after the reacted lignocellulosic feedstock is discharged from the reaction zone.

25. The method of claim 24, including the step of reducing the pressure of the reacted lignocellulosic feedstock to atmospheric pressure.

26. The method of claim 6, wherein the partially dewatered lignocellulosic feedstock has a weight ratio of water to dry lignocellulosic feedstock solids of about 0.5:1 to about 5:1.

27. The method of claim 26, wherein the plug of lignocellulosic feedstock at the outlet zone of the dewatering zone has a weight ratio of water to dry lignocellulosic feedstock solids of about 0.5:1 to about 5:1.

28. The method of claim 27, wherein the pressure of the aqueous slurry of the lignocellulosic feedstock at the inlet of the dewatering zone is about 70 psia to about 800 psia.

29. The method of claim 28, wherein the pressure of the aqueous liquid withdrawn from the dewatering zone is about 1 psia to about 50 psia lower than the pressure of the aqueous slurry of the lignocellulosic feedstock at the inlet zone of the dewatering zone.

30. The method of claim 28, wherein the pH in the reaction zone is between about 0.2 and about 3.0.

31. The method of claim 30, wherein the lignocellulosic feedstock is held in the reaction zone for suitable time of about 10 seconds to about 180 seconds at a suitable temperature of about 180° C. to about 260° C. to pretreat the lignocellulosic feedstock.

32. The method of claim 6, wherein the partially dewatered lignocellulosic feedstock is heated prior to its entry into the reaction zone, in the reaction zone or a combination thereof.

33. The method of claim 32, wherein the partially dewatered lignocellulosic feedstock is at least partly heated by direct steam injection prior to its entry into the reaction zone, in the reaction zone or a combination thereof.

34. The method of any one of claims 1 to 5, wherein the pressure of the aqueous slurry of the lignocellulosic feedstock at the inlet of the dewatering zone is about 70 psia to about 900 psia.

35. The method of claim 34, wherein the pressure of the aqueous liquid withdrawn from the dewatering zone is about 0.3 psia to about 50 psia lower than the pressure of the aqueous slurry of the lignocellulosic feedstock at the inlet zone of the dewatering zone.

36. The method of claim 34, wherein the pH in the reaction zone is between 0 and about 3.0.

37. The method of claim 36, wherein acid is added to the lignocellulosic feedstock prior to the entry of the plug of the lignocellulosic feedstock into the reaction zone.

38. The method of claim 37, wherein acid that is added to the lignocellulosic feedstock is selected from the group consisting of sulfuric acid, sulfurous acid, hydrochloric acid, phosphoric acid or any combination thereof.

39. The method of claim 38, wherein acid that is added to the lignocellulosic feedstock is sulfuric acid.

40. The method of claim 36, wherein acid is added to the reaction zone.

41. The method of claim 36, wherein the lignocellulosic feedstock is held in the reaction zone for suitable time of about 10 seconds to about 600 seconds at a suitable temperature of about 180° C. to about 260° C. to pretreat the lignocellulosic feedstock.

* * * * *

UNITED STATES PATENT AND TRADEMARK OFFICE
CERTIFICATE OF CORRECTION

| | |
|---|---|
| PATENT NO. | : 8,328,947 B2 |
| APPLICATION NO. | : 12/548718 |
| DATED | : December 11, 2012 |
| INVENTOR(S) | : Vijay Kumar Anand et al. |

It is certified that error appears in the above-identified patent and that said Letters Patent is hereby corrected as shown below:

In the Specifications:

COLUMN 2:

Line 14, "of" should read --to--.

COLUMN 3:

Line 53, "psia" should read --psia;--.

COLUMN 4:

Line 33, "psia" should read --psia;--.

COLUMN 5:

Line 11, "psia" should read --psia;--.

COLUMN 7:

Line 52, "invention" should read --invention.--.

COLUMN 13:

Line 53, "disrupts" should read --disrupt--.

Page 1 of 3

Signed and Sealed this
Sixteenth Day of April, 2013

Teresa Stanek Rea
*Acting Director of the United States Patent and Trademark Office*

COLUMN 15:

Line 10-15, "Acidic hydrolysis that is harsh enough to hydrolzye xylan and cellulose may be conducted for about 10 seconds to about 20 minutes, or any time therebetween. The temperature may be between about 180° C. and about 260° C., or any temperature therebetween. The pH may be between 0 and about 1 or any pH therebetween." (duplicate) should read --Alkali hydrolysis that is harsh enough to hydrolyze xylan and cellulose may be conducted at about 125°C to about 260°C, or about 135°C to about 260°C, or about 125°C to about 180°C, or any temperature therebetween, for about 30 minutes to about 120 minutes, or any time therebetween and at about pH 13 to about 14, or any pH therebetween.--

COLUMN 16:

Line 10, "Saccharomyces" should be italicized; and
Line 11, "cerevisiae" should be italicized.

COLUMN 17:

Line 39, "fibre" should read --fiber--.

COLUMN 18:

Line 9, "pipe-line" should read --pipeline--.

COLUMN 21:

Line 19, "comprise" should read --comprises--; and
Line 23, "reduce" should read --reduces--.

In the Claims:

COLUMN 24:

Line 57, "psai" should read --psai;--; and
Line 64, "zone" should read --zone;--.

COLUMN 25:

Line 35, "psai" should read --psai;--.

COLUMN 26:

Line 12, "psai" should read --psai;--;
Line 59, "(Pdwi)" should read --($P_{dwi}$)--;
Line 61, "Pr" should read -- $P_r$--; and
Line 65, "Pr and Pdwi" should read --$P_r$ and $P_{dwi}$-- and "psai" should read -- psai;--.

COLUMN 27:

Line 45, "psai" should read --psai;--.

COLUMN 30:

Line 8, "claims 1 to 5," should read --claims 1, 2 or 5,--.